United States Patent
DeLano-Taylor et al.

(10) Patent No.: US 11,111,279 B2
(45) Date of Patent: Sep. 7, 2021

(54) NATO3 MUTANT POLYPEPTIDES AND USES THEREOF

(71) Applicant: Grand Valley State University, Allendale, MI (US)

(72) Inventors: Merritt DeLano-Taylor, Grand Rapids, MI (US); Jordan Straight, Spring Lake, MI (US); Doug Peterson, Ravenna, MI (US); Nick Huisingh, Muskegon, MI (US); Daniel Doyle, Freeland, MI (US)

(73) Assignee: GRAND VALLEY STATE UNIVERSITY, Allendale, MI (US)

( * ) Notice: Subject to any disclaimer, the term of this patent is extended or adjusted under 35 U.S.C. 154(b) by 285 days.

(21) Appl. No.: 15/776,580

(22) PCT Filed: Nov. 18, 2016

(86) PCT No.: PCT/US2016/062876
§ 371 (c)(1),
(2) Date: May 16, 2018

(87) PCT Pub. No.: WO2017/087866
PCT Pub. Date: May 26, 2017

(65) Prior Publication Data
US 2018/0346530 A1    Dec. 6, 2018

Related U.S. Application Data

(60) Provisional application No. 62/258,043, filed on Nov. 20, 2015.

(51) Int. Cl.
*A61K 38/00* (2006.01)
*C07K 14/47* (2006.01)
*C12N 5/0793* (2010.01)

(52) U.S. Cl.
CPC ........ *C07K 14/4702* (2013.01); *C12N 5/0619* (2013.01); *A61K 38/00* (2013.01); *C12N 2501/40* (2013.01)

(58) Field of Classification Search
None
See application file for complete search history.

(56) References Cited

U.S. PATENT DOCUMENTS

| | | | |
|---|---|---|---|
| 7,470,673 | B2 | 12/2008 | Zoghbi et al. |
| 8,067,161 | B2 | 11/2011 | Ono et al. |
| 8,198,081 | B2 | 6/2012 | Ono et al. |
| 8,241,902 | B2 | 8/2012 | Itskovitz-Eldor et al. |
| 8,252,755 | B2 | 8/2012 | Yamada et al. |
| 8,501,706 | B2 | 8/2013 | Yamada et al. |
| 8,541,234 | B2 | 9/2013 | Itskovitz-Eldor et al. |
| 8,604,173 | B2 | 12/2013 | Ono et al. |
| 8,912,157 | B2 | 12/2014 | Collard et al. |
| 8,985,057 | B2 | 3/2015 | Woodward |
| 2004/0231009 | A1 | 11/2004 | Zoghbi et al. |
| 2010/0028866 | A1* | 2/2010 | Ono ........................ C07K 14/47 435/6.16 |
| 2012/0021417 | A1 | 1/2012 | Ono et al. |
| 2013/0131194 | A1 | 5/2013 | Skog et al. |
| 2014/0045915 | A1 | 2/2014 | Skog et al. |
| 2014/0058214 | A1 | 2/2014 | Woodward |
| 2014/0155271 | A1 | 6/2014 | Hatchwell et al. |
| 2014/0193827 | A1 | 7/2014 | Schwartz et al. |
| 2014/0194319 | A1 | 7/2014 | Skog et al. |
| 2014/0194613 | A1 | 7/2014 | Skog et al. |
| 2014/0242580 | A1 | 8/2014 | Yu et al. |
| 2014/0350000 | A1 | 11/2014 | Brennan et al. |
| 2015/0023927 | A1 | 1/2015 | Eggan et al. |
| 2015/0057338 | A1 | 2/2015 | Collard et al. |

FOREIGN PATENT DOCUMENTS

| | | | | |
|---|---|---|---|---|
| EP | 1950292 A1 | 7/2008 | | |
| JP | 2003530817 A | 10/2003 | | |
| JP | 2011062204 A | 3/2011 | | |
| WO | WO-0171042 A2 * | 9/2001 | ........... | C12Q 1/6876 |
| WO | 2002068579 A2 | 9/2002 | | |
| WO | WO-2014037527 A1 * | 3/2014 | ........... | C12N 5/0618 |

OTHER PUBLICATIONS

Segev et al (Meeh Dev 106: 197-202, 2001).*
Freed, "Will embryonic stem cells be a useful source of dopamine neurons for transplant into patients with Parkinson's disease?", PNAS, 99(4):1755-1757, 2002.
Huangfu et al., "Induction of pluripotent stem cells by defined factors is greatly improved by small molecule compounds", Nat Biotechnol., 26(7):795-797, 2008.
Kim et al., "Generation of Human Induced Pluripotent Stem Cells by Direct Delivery of Reprogramming Proteins", Cell Stem Cell., 4(6):472-476, 2009.
Nakagawa et al., "Generation of induced pluripotent stem cells without Myc from mouse and human fibroblasts", Nat Biotechnol., 26(1):101-106, 2008.

(Continued)

*Primary Examiner* — Daniel E Kolker
*Assistant Examiner* — Aditi Dutt
(74) *Attorney, Agent, or Firm* — Honigman LLP; Douglas H. Siegel; Fernando Alberdi

(57) ABSTRACT

The present invention relates to isolated Nato3 mutant polypeptides. Methods for stimulating a brain cell to differentiate into a dopaminergic progenitor neuronal cell or a dopaminergic neuron comprises increasing phosphorylation of Nato3 in the brain cells and culturing the brain cells until a progenitor dopaminergic neuronal cell marker or a dopaminergic neuronal cell marker is expressed in the cultured brain cells. Methods for treating Parkinson's disease (PD) in a subject comprises administering to the subject in need thereof, a composition comprising progenitor dopaminergic neuronal cells and/or dopaminergic neuronal cells expressing a Nato3 mutant polypeptide to the brain of the subject.

20 Claims, 8 Drawing Sheets
Specification includes a Sequence Listing.

(56) References Cited

OTHER PUBLICATIONS

Rhee et al., "Protein-based human iPS cells efficiently generate functional dopamine neurons and can treat a rat model of Parkinson disease", The Journal of Clinical Investigation, 121(6):2326-2335, 2011.
Rouaux and Arlotta, "Direct lineage reprogramming of postmitotic callosal neurons into corticofugal neurons in vivo", Nat Cell Biol., 15(2):214-221, 2013.
Segev et al., "Nato3 is an evolutionarily conserved bHLH transcription factor expressed in the CNS of Drosophila and mouse", Mechanisms of Development, 106:197-202, 2001.
Shu et al., "Induction of Pluripotency in Mouse Somatic Cells with Lineage Specifiers", Cell, 153(5):963-975, 2013.
Stenevi et al., "Transplantation of central and peripheral monoamine neurons to the adult rat brain: techniques and conditions for survival", Brain Res, 114(1):1-20, 1976 (Abstract only).
Takahashi et al., "Induction of Pluripotent Stem Cells from Adult Human Fibroblasts by Defined Factors", Cell, 131:861-872, 2007.
Verzi et al., "N-Twist, an Evolutionarily Conserved bHLH Protein Expressed in the Developing CNS, Functions as a Transcriptional Inhibitor", Developmental Biology, 249:174-190, 2002.
Wan et al., "Meta-prediction of phosphorylation sites with weighted voting and restricted grid search parameter selection", Nucleic Acids Research, 36(4)e22:1-11, 2008.
PCT International Search Report, PCT/US2016/062876, dated Mar. 3, 2017 (5 pages).
Huisingh and Taylor, "Phosphomimetic mutants of bHLH transcription factor Nato3 promote profound changes in expression of genes compared to WT", Student Summer Scholars Grand Valley State University, 2015, abstract, one page.
Kaufman, "Determining the Sufficiency of the bHLH Gene Nato3 in Dopamine Neurogenesis", Masters Thesis, Grand Valley State University, 2012, pp. 1-62.
Ono et al., "The basic helix-loop-helix transcription factor Nato3 controls neurogenic activity in mesencephalic floor plate cells", Development, 137:1897-1906, 2010.
Nissim-Eliraz et al., "Nato3 Integrates with the Shh-Foxa2 Transcriptional Network Regulating the Differentiation of Midbrain Dopaminergic Neurons", J Mol Neurosci, 51(1):13-27, 2012.

* cited by examiner

NATO3 MUTANT POLYPEPTIDES AND USES THEREOF

CROSS-REFERENCE TO RELATED APPLICATIONS

This Patent Application is a 35 U.S.C. § 371 United States National Phase Stage of, and claims the benefit of PCT International Application No. PCT/US2016/062876 filed Nov. 18, 2016, which claims the benefit under 35 U.S.C. § 119 of U.S. Provisional Application No. 62/258,043 filed on Nov. 20, 2015. The entire contents of the aforementioned applications are incorporated herein by reference.

INCORPORATION BY REFERENCE OF MATERIAL SUBMITTED ELECTRONICALLY

Incorporated by reference in its entirety is a computer-readable sequence listing submitted concurrently herewith and identified as follows: One 34 KB ASCII (Text) file named "2021-02-23_232146-402967_Sequence_Listing_ST25.txt" and created on Feb. 23, 2021.

TECHNICAL FIELD

The present invention relates generally to isolated Nato3 mutant polypeptides and polynucleotides encoding such polypeptides. The present invention also relates to methods of stimulating progenitor neuron cells to become dopaminergic progenitor neuronal cells and mature dopaminergic neurons and uses of these Nato3 mutant polypeptides or polynucleotides encoding these Nato3 mutant polypeptides to treat various neurodegenerative diseases and disorders.

BACKGROUND

The floor plate of the developing midbrain gives rise to dopaminergic (DA) neurons, an important class of neurons affected by Parkinson's disease (PD). Nato3, a basic helix-loop-helix (bHLH) transcription factor, is expressed in the floor plate region of the midbrain and spinal cord during development (Segev et al., 2001; Verzi et al., 2002). In the spinal cord, Nato3 has been shown to be essential for the maturation of classical non-neurogenic floor plate cells (cFPs); however, in the mesencephalon, Nato3 is necessary for the generation of DA neurons by floor plate cells in the midbrain (mFP)(Ono et al., 2010). To monitor the capacity of a gene to convert a progenitor to commit to a certain lineage, such as floor plate cells, dopamine neuron progenitor or dopamine neurons, cell lineage markers are often used (see FIG. 1).

Efforts to utilize neuron progenitor cells as a source of dopaminergic neurons for the purpose of transplantation has provided mixed results. Transplantation of neuron progenitor cells is problematic due to the relatively small numbers of autologous progenitor stems cells available for ex-vivo culturing. Moreover, additional issues arise because the neuron progenitor cells may differentiate into non-uniform cell populations. For example, in the treatment of PD, it is necessary that dopaminergic neurons are selectively transplanted and do not contain catecholamine-expressing neurons. Prior to the present application, transplantable cells for the use in treating PD, have been predominantly limited to cells that have not uniformly terminally differentiated into dopaminergic neurons. However, none of these contains pure dopaminergic neurons or cells to differentiate into dopaminergic neurons.

Existing methods for transplantation treatment of PD involve the use of dopaminergic progenitor neuronal cells. Clinical studies in which human fetal mesencephalic tissue, rich in dopaminergic neuroblasts, have been previously transplanted into the striatum of individuals with PD have shown in principle that dopaminergic neurons may be replaced and symptoms reduced in some cases. But the functional outcome of this treatment has proved highly variable, and human fetal tissue is scarce, suggesting that other sources of dopaminergic neurons are needed to develop a clinically useful cell therapy. These dopaminergic progenitor neuronal cells may be derived from the midbrain ventral region of aborted fetus tissue or they may be induced to differentiate into neuron progenitor cells.

The most successful means for producing functional dopaminergic substantia nigra neurons for transplantation in Parkinson's disease to date involves deriving terminally differentiated dopaminergic neurons from human embryonic stem cells (hESCs). In these methods, floor plate cells are derived in vitro from hESCs by dual inhibition of SMAD signaling and high levels of sonic hedgehog. Midbrain floor plate identity is induced by activation of WNT signaling, and dopaminergic neuron precursors are generated in the presence of trophic factors, ascorbic acid, cAMP and DAPT. After intrastriatal transplantation in mice, rats or non-human primates, these cells give rise to large numbers of dopaminergic neurons with a substantia nigra phenotype, which reinnervate the striatum and ameliorate behavioral deficits in non-human subjects resembling the symptoms in PD patients. However, in these cases of transplantation, it is important to prevent differentiation of these embryonic stem cells into serotonergic neurons and tumors after transplantation.

It would be desirable from a treatment perspective, to provide cell-based therapies using a more homogeneous population of progenitor cells and convenient and straight-forward methods for generating these more pure phenotypically related dopaminergic progenitor cells and dopamine producing neurons.

SUMMARY

In one aspect of the present invention, isolated mutant Nato3 polypeptides are provided. In various embodiments, the Nato3 mutant polypeptides comprise at least one mutation in any one or more amino acids serine, threonine or tyrosine residues as set forth in SEQ ID NOs:1-5, or any variant, derivative, or ortholog thereof. In one embodiment, the isolated mutant Nato3 polypeptide comprises at least one mutation in any one or more serine, threonine or tyrosine amino acid residues in the HLH domain defined by amino acids 99 to 158 of SEQ ID NOs: 1-5. For example, in some embodiments, isolated mutant Nato3 polypeptides of the present invention can include mutant Nato3 polypeptides wherein at least one mutation of the one or more serine, threonine or tyrosine residues occurs in the HLH domain of the Nato3 wild type sequences of SEQ ID NO: 1 or 2. In various embodiments, the one or more mutations comprises a substitution of amino acids serine or threonine in the HLH domain of the wild type Nato3 amino acid sequence of SEQ ID NO: 1, or 2, with either aspartic acid or glutamic acid.

In related embodiments, the Nato3 mutant polypeptides of the present invention may also include Nato3 mutant polypeptides that have at least one mutation which occurs in the HLH domain defined by amino acid sequences 99 to 158 of SEQ ID NOs: 1-5, for example in human wild type Nato3, as set forth in SEQ ID NO: 1. In these embodiments, the mutation to any one or more of threonine, tyrosine and serine may occur at positions 99, 100, 101, 102, 104, 116, 117, 130, 132, 133, 135, 138, 140, 142, 144, 147, 149, 150, 151, 154, 155, 156 relative to a wild-type sequence of Nato3 as set forth in SEQ ID NOs:1-5. In some embodiments, the one or more mutations may occur at any one or more positions, for example, at position 99, 100, 130, 133, 138, 142, 144, 149, 151, 154, or combinations thereof, relative to the wild-type sequence of Nato3 as set forth in SEQ ID NO: 1.

In some embodiments, the Nato3 mutant polypeptides of the present invention may also include Nato3 mutant polypeptides that have at least one mutation which occurs in the HLH domain defined by amino acid sequences 99 to 158 of SEQ ID NOs: 1-2, for example in human wild type Nato3, as set forth in SEQ ID NO: 1. In these embodiments, the mutation to any one or more of threonine, tyrosine and serine, amino acid residues at positions 99, 100, 101, 102, 104, 116, 117, 130, 132, 133, 135, 138, 140, 142, 144, 147, 149, 150, 151, 154, 155, 156 relative to a wild-type sequence of Nato3 as set forth in SEQ ID NOs:1-5, with the proviso, that in some embodiments, the mutant Nato3 polypeptide cannot be one that has a mutation at position S140 that is substituted with the amino acid aspartic acid i.e. a (S140D) mutation of wild type mouse Nato3 as shown in SEQ ID NO:2.

In some embodiments, the substitute amino acid may be any amino acid other than the wild-type amino acid at their respective position. For example, the amino acid at any one or more threonine, tyrosine and serine amino acids at positions 99, 100, 101, 102, 104, 116, 117, 130, 132, 133, 135, 138, 140, 142, 144, 147, 149, 150, 151, 154, 155, 156 relative to a wild-type sequence of Nato3 as set forth in SEQ ID NOs:1-5 may be substituted with any amino acid other than the wild type amino acid at that position. For example, a wild type amino acid at any one or more positions selected from 99, 100, 101, 102, 104, 116, 117, 130, 132, 133, 135, 138, 140, 142, 144, 147, 149, 150, 151, 154, 155, 156 relative to a wild-type sequence of Nato3 as set forth in SEQ ID NOs:1-5 may be substituted with a negatively charged amino acid, for example, glutamate (glutamic acid, E) or aspartate (aspartic acid, D).

In some embodiments, the one or more amino acids at position 99, 100, 130, 133, 138, 142, 144, 149, 151, 154, or combinations thereof, relative to the wild-type sequence of Nato3 as set forth in SEQ ID NO: 1 is substituted with a negatively charged amino acid, for example, glutamate (glutamic acid, E) or aspartate (aspartic acid, D). In some embodiments, the Nato3 mutant polypeptide has one or more mutations at positions 99, 130, and/or 138, or any combination thereof, relative to SEQ ID NO:1. The substitute amino acid may be any amino acid other than the wild-type amino acid at that position.

In some embodiments, the present invention provides a Nato3 mutant polypeptide having an amino acid sequence as set forth in SEQ ID NO:1, wherein wild type amino acid 99 (threonine) is replaced with a negatively charged amino acid, for example, D or E. In another embodiment, the present invention provides a Nato3 mutant polypeptide having an amino acid sequence as set forth in SEQ ID NO:1, wherein wild type amino acid 130 (threonine) is replaced with a negatively charged amino acid, for example, D or E. In another embodiment, the present invention provides a Nato3 mutant polypeptide having an amino acid sequence as set forth in SEQ ID NO:1, wherein wild type amino acid 138 (serine) is replaced with a negatively charged amino acid, for example, D or E. In some embodiments, a Nato3 mutant polypeptide may have two or three amino acid substitutions at positions 99, 130 and 138 relative to wild type Nato3 sequence of SEQ ID NO:1. For example, the amino acid substitution comprises substitution of the two or three wild type amino acids at positions 99, 130, and 138 with a negatively charged amino acid, for example, D or E.

In a second aspect, the present invention provides a method for stimulating a population of brain cells to differentiate into progenitor dopaminergic neuronal cells, or dopamine neurons, the method comprising increasing phosphorylation of Nato3 in the brain cells and culturing the brain cells until a progenitor dopaminergic neuronal cell marker, or a dopamine neuron cell marker is expressed in the cultured brain cells. In related embodiments, the method includes increasing phosphorylation of Nato3 in the brain cells by expressing a Nato3 mutant polypeptide in the brain cells or by increasing the expression of a protein kinase that specifically phosphorylates an endogenous Nato3 polypeptide.

In a third aspect, the present invention provides a method for treating or preventing PD in a subject in need thereof. The method includes the steps of administering to the subject, a therapeutically effective amount of a composition comprising a mutant Nato3 polypeptide, or a polynucleotide construct encoding the mutant Nato3 polypeptide. In various embodiments, the composition comprising the mutant Nato3 polypeptide or a polynucleotide construct encoding the mutant Nato3 polypeptide includes a population of dopaminergic progenitor neuronal cells, and/or a population of dopaminergic neurons comprising the mutant Nato3 polypeptide or a polynucleotide construct encoding the mutant Nato3 polypeptide. In another embodiment, the method comprises administering to the subject in need thereof, a recombinant construct encoding a protein kinase that targets Nato3 in a brain cell, and increases phosphorylation of Nato3.

In some of these embodiments, the brain cells may differentiate into dopaminergic progenitor neuronal cells and/or dopaminergic neurons. In various embodiments, the brain cells comprising a mutant Nato3 polypeptide or a polynucleotide construct encoding the mutant Nato3 polypeptide are transplanted directly into the subject's striatum to replace damaged dopaminergic neurons, reinnervate the striatum, and restore dopamine release in the brain of the PD subject.

In some related embodiments, the brain cells which are targeted for expression of a mutant Nato3 polypeptide or administered a polynucleotide construct encoding the mutant Nato3 polypeptide, or a protein kinase that specifically targets and increases the phosphorylation of Nato3, include stem cells, including embryonic stem cells, adult induced pluripotent stem cells, mesenchymal stem cells and other tissue stem cells that may be implanted into the brain of a PD patient for generation of dopaminergic progenitor neuron cells and/or dopaminergic neurons.

Figure 1:
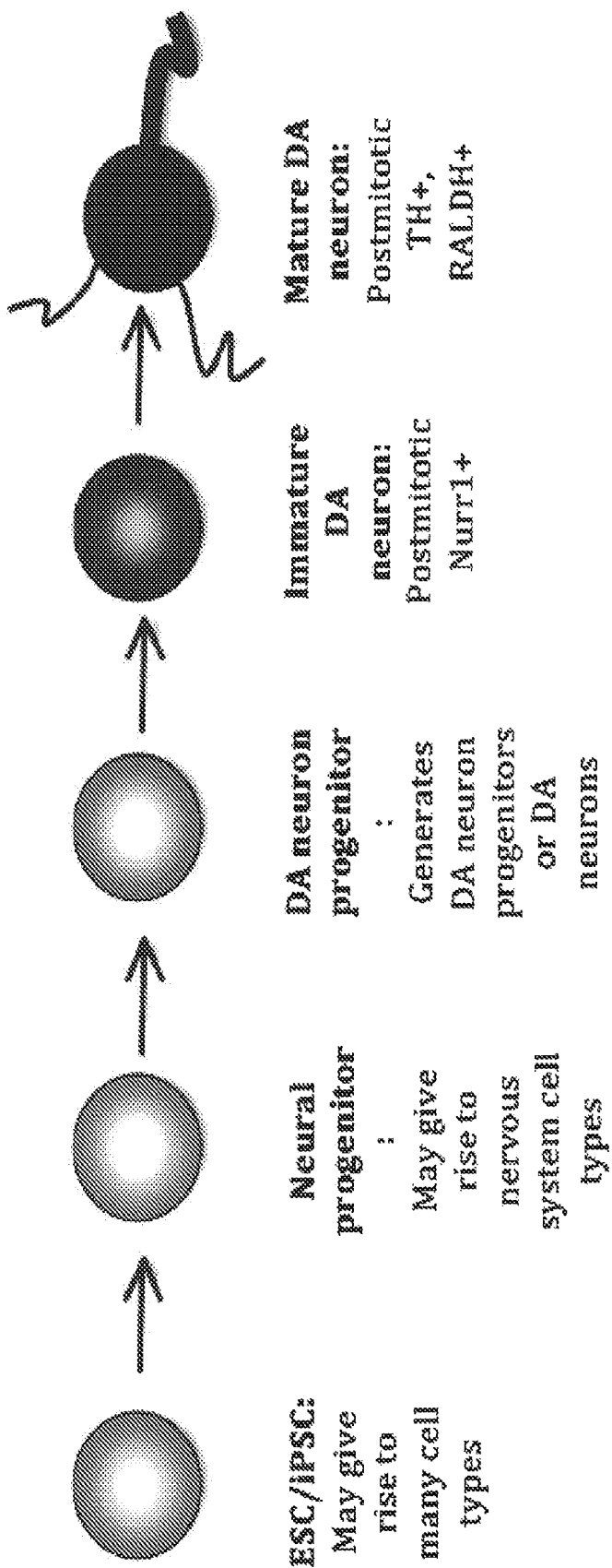
FIG. 1 shows a schematic diagram of the progression of specification of neural progenitors and maturation of DA neurons.
Figure 2:
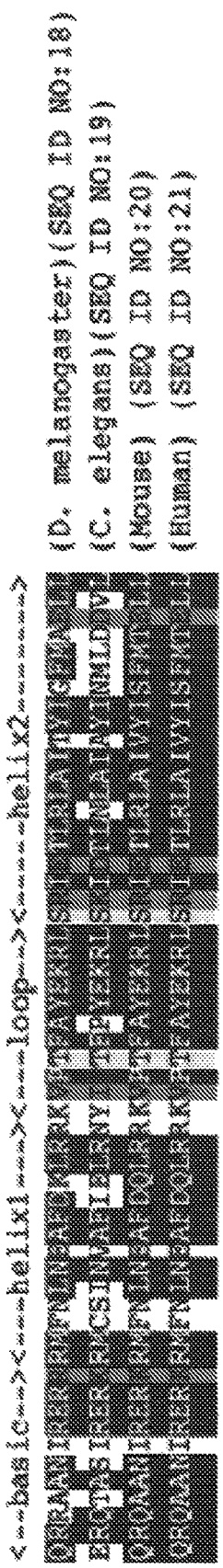
FIG. 2 depicts amino acid sequence homology of Nato3 basic helix loop helix (HLH) domain and other bHLH family members. Nato3 from multiple different species MNato3 (Mouse) DNato3 (*Drosophila*), CNato3 (chicken), HNato3 (Human) are shown at the top. Perfect homology is shown in black, functional homology is shown in grey, overall homology with DNato3 is shown on the left (similarity (sim), percent similarity) Amino acids that align with mouse Nato3 at positions T132 and S140 are highlighted.

These figures are provided by way of example and are not intended to limit the scope of the invention.

DETAILED DESCRIPTION

Definitions

For purposes of this disclosure, unless defined otherwise, technical and scientific terms used herein have the same meaning as commonly understood by one of ordinary skill in the art to which this invention belongs. See, e.g. Singleton et al., Dictionary of Microbiology and Molecular Biology 2nd ed., J. Wiley & Sons (New York, N.Y. 1994); Sambrook et al., Molecular Cloning, A Laboratory Manual, Cold Spring Harbor Press (Cold Spring Harbor, N.Y. 1989). These references are hereby incorporated into this disclosure by reference in their entireties.

Before the present compositions and methods are described, it is to be understood that any invention is not limited to the particular processes, compositions, or methodologies described, as these may vary. Moreover, the processes, compositions, and methodologies described in particular embodiments are interchangeable. Therefore, for example, a composition, dosage regimen, route of administration, and so on described in a particular embodiment may be used in any of the methods described in other particular embodiments. It is also to be understood that the terminology used in the description is for the purpose of describing the particular versions or embodiments only, and is not intended to limit the scope of the present invention, which will be limited only by the appended claims. Unless clearly defined otherwise, all technical and scientific terms used herein have the same meanings as commonly understood by one of ordinary skill in the art. Although any methods similar or equivalent to those described herein may be used in the practice or testing of embodiments of the present invention, the preferred methods are now described. All publications and references mentioned herein are incorporated by reference herein. Nothing herein is to be construed as an admission that the invention is not entitled to antedate such disclosures by virtue of prior invention.

It must be noted that, as used herein, and in the appended claims, the singular forms "a", "an", and "the" include plural reference unless the context clearly dictates otherwise.

Embodiments including the transition phrase "consisting of" or "consisting essentially of" include only the recited components and inactive ingredients. For example, a composition "consisting essentially of" a Nato3 mutant polypeptide may include a Nato3 mutant polypeptide and inactive excipients, which may or may not be recited, but may not contain any additional active agents. A composition "consisting of" a Nato3 mutant polypeptide may include only the components specifically recited.

As used herein, the term "about" means plus or minus 10% of the numerical value of the number with which it is being used. Therefore, about 50% means in the range of 45%-55%, and all values therebetween.

"Optional" or "optionally" may be taken to mean that the subsequently described structure, event or circumstance may or may not occur, and that the description includes both instances where the event occurs and instances where it does not.

"Administering", when used in conjunction with a therapeutic, means to administer a therapeutic composition directly into or onto a target tissue or to administer a therapeutic composition to a subject whereby the therapeutic composition positively impacts the tissue to which it is targeted. "Administering" a composition may be accomplished by oral administration, injection, infusion, absorption or by any method in combination with other known techniques. "Administering" may include the act of self-administration or administration by another person such as a healthcare provider or a device.

As used herein, the term "therapeutic" means an agent utilized to treat, combat, ameliorate, or prevent, or any combination thereof, an unwanted condition or disease of a subject.

As used herein, the term "effective amount" refers to the amount of a composition (e.g., a Nato3 mutant polypeptide) sufficient to effect beneficial or desired results. An effective amount may be administered in one or more administrations, applications or dosages and is not intended to be limited to a particular formulation or administration route. An effective amount may include a therapeutically effective amount, or a non-therapeutically effective amount.

The terms "therapeutically effective amount" or "therapeutic dose" as used herein are interchangeable and may refer to the amount of an active agent or pharmaceutical compound or composition that elicits a biological and/or medicinal response in a tissue, system, animal, individual or human that is being sought by a researcher, veterinarian, medical doctor or other clinician, or any combination thereof. A biological or medicinal response may include, for example, one or more of the following: (1) preventing a disorder, disease, or condition in an individual that may be predisposed to the disorder, disease, or condition but does not yet experience or display pathology or symptoms of the disorder, disease, or condition, (2) inhibiting a disorder, disease, or condition in an individual that is experiencing or displaying the pathology or symptoms of the disorder, disease, or condition or arresting further development of the pathology and/or symptoms of the disorder, disease, or condition, and/or (3) ameliorating a disorder, disease, or condition in an individual that is experiencing or exhibiting the pathology or symptoms of the disorder, disease, or condition or reversing the pathology and/or symptoms disorder, disease, or condition experienced or exhibited by the individual.

Isolated" when referred to a molecule, refers to a molecule that has been identified and separated and/or recovered from a component of its natural environment and thus is altered "by the hand of man" from its natural state. The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide (1) is not associated with proteins found in nature, (2) is free of other proteins from the same source, e.g., free of human proteins, (3) is expressed by a cell from a different species, or (4) does not occur in nature. In contrast, non-isolated polypeptides (e.g., proteins and enzymes) are found in the state they exist in nature. The terms "isolated polypeptide", "isolated peptide" or "isolated protein" include a polypeptide, peptide or protein encoded by cDNA or recombinant RNA including one of synthetic origin, or some combination thereof.

The term "amino acid" not only encompasses the 20 common amino acids in naturally synthesized proteins, but also includes any modified, unusual, or synthetic amino acid. One of ordinary skill in the art would be familiar with modified, unusual, or synthetic amino acids.

As used herein, a "polynucleotide" refers to a molecule having a nucleic acid sequence. In some embodiments, a polynucleotide includes a nucleic acid, whether single stranded or double stranded, in which the strand or one nucleic acid strand encodes one or more Nato3 mutant polypeptides or a fragment or variant thereof, e.g. a nucleic acid sequence contained in SEQ ID NO:6-11 or the complement sequence thereof. For example, the polynucleotide may contain the nucleotide sequence of the full-length cDNA sequence, including the 5' and 3' untranslated sequences, the coding region, as well as fragments, epitopes, domains, and variants of the nucleic acid sequence. Moreover, as used herein, a "polypeptide" refers to a molecule having an amino acid sequence encoded by a polynucleotide of the invention as broadly defined. As used herein, the term "fragment" as applied to a nucleic acid, may ordinarily be at least about 10 nucleotides in length, typically, at least about 20 nucleotides, more typically, from about 20 to about 50 nucleotides, preferably at least about 50 to about 100 nucleotides, even more preferably at least about 100 nucleotides to about 300 nucleotides, yet even more preferably at least about 300 to about 400, and most preferably, the nucleic acid fragment will be greater than about 500 nucleotides in length.

"Nucleic acid molecule", includes DNA molecules (e.g. cDNA or genomic DNA), RNA molecules (e.g., mRNA), analogs of the DNA or RNA generated using nucleotide analogs, and derivatives, fragments and homologs. The nucleic acid molecule may be single-stranded or double-stranded, but preferably comprises double-stranded DNA.

"Isolated nucleic acid molecule" is separated from other nucleic acid molecules which are present in the natural source of the nucleic acid. Preferably, an isolated nucleic acid is free of sequences that naturally flank the nucleic acid (i.e. sequences located at the 5'- and 3'-termini of the nucleic acid) in the genomic DNA of the organism from which the nucleic acid is derived. For example, in various embodiments, isolated Nato3 mutant DNA molecules may contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue from which the nucleic acid is derived (e.g., brain, heart, liver, spleen, etc.). Moreover, an isolated nucleic acid molecule, such as a cDNA molecule, may be substantially free of other cellular material or culture medium when produced by recombinant techniques, or of chemical precursors or other chemicals when chemically synthesized.

The term "wild-type" or "native" (used interchangeably) refers to the naturally-occurring polynucleotide sequence encoding a Nato3 protein, or a portion thereof, or a Nato3 polypeptide sequence, or portion thereof, respectively, as it normally exists in vivo.

The term "mutant" refers to any change in the genetic material of an organism, in particular a change (i.e., deletion, substitution, addition, or alteration) in a wild-type polynucleotide sequence or any change in a wild-type protein sequence. The term "variant" is used interchangeably with "mutant". Although it is often assumed that a change in the genetic material results in a change of the function of the protein, the terms "mutant" and "variant" refer to a change in the sequence of a wild-type protein regardless of whether that change alters the function of the protein (e.g., increases, decreases, imparts a new function), or whether that change has no effect on the function of the protein (e.g., the mutation or variation is silent).

"Analogs" are nucleic acid sequences or amino acid sequences that have a structure similar to, but not identical to, the native compound but differ from it in respect to certain components or side chains. Analogs may be synthetic or from a different evolutionary origin and may have a similar or opposite metabolic activity compared to wild-type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90% or 95% identity (with a preferred identity of 80-95%) over a nucleic acid or amino acid sequence of identical size or when compared to an aligned sequence in which the alignment is done by a computer homology program known in the art or whose encoding nucleic acid is capable of hybridizing to the complement of a sequence encoding the aforementioned proteins under stringent, moderately stringent, or low stringent conditions (Ausubel et al., supra).

The terms "encoding" or "encodes" refer to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, may be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anticodon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Control sequences" are DNA sequences that enable the expression of an operably-linked coding sequence in a particular host organism. Prokaryotic control sequences include promoters, operator sequences, and ribosome binding sites. Eukaryotic cells utilize promoters, polyadenylation signals, and enhancers.

"Operably-linked nucleic acid" is operably-linked when it is placed into a functional relationship with another nucleic acid sequence. For example, a promoter or enhancer is operably-linked to a coding sequence if it affects the transcription of the sequence, or a ribosome-binding site is operably-linked to a coding sequence if positioned to facilitate translation. Generally, "operably-linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "genomic DNA" is a DNA strand, which has a nucleotide sequence homologous with a gene. By way of example, both a fragment of a chromosome and a cDNA derived by reverse transcription of a mammalian mRNA are genomic DNAs.

"Oligonucleotide" comprises a series of linked nucleotide residues, which oligonucleotide has a sufficient number of nucleotide bases to be used in a PCR reaction or other application. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

"Stringency". Homologs (i.e., nucleic acids encoding Nato3 mutant polypeptides molecules derived from species other than human) or other related sequences (e.g., paralogs) may be obtained by low, moderate or high stringency hybridization with all or a portion of the particular human sequence as a probe using methods well known in the art for nucleic acid hybridization and cloning.

The specificity of single stranded DNA to hybridize complementary fragments is determined by the "stringency" of the reaction conditions. Hybridization stringency increases as the propensity to form DNA duplexes decreases. In nucleic acid hybridization reactions, the stringency may be chosen to either favor specific hybridizations (high stringency), which may be used to identify, for example, full-length clones from a library.

Less-specific hybridizations (low stringency) may be used to identify related, but not exact, DNA molecules (homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide which decreases DNA duplex stability. In general, the longer the probe, the higher the temperature required for proper annealing. A common approach is to vary the temperature: higher relative temperatures result in more stringent reaction conditions. (Ausubel et al., supra) provide an excellent explanation of stringency of hybridization reactions.

PCR amplification techniques may be used to amplify Nato3 mutant polypeptide encoding polynucleotides using cDNA, mRNA or alternatively, genomic DNA, as a template and appropriate oligonucleotide primers. Such nucleic acids may be cloned into an appropriate vector and characterized by DNA sequence analysis. Furthermore, oligonucleotides corresponding to Nato3 mutant polypeptides encoding polynucleotides may be prepared by standard synthetic techniques, e.g., an automated DNA synthesizer.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded.

Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers may be labeled with, e.g., chromogenic, radioactive, or fluorescent moieties and used as detectable moieties.

By the term "vector" as used herein, is meant any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector, which is suitable as a delivery vehicle for delivery of the nucleic acid encoding the desired protein, or mutant thereof to a cell, or the vector may be a non-viral vector, which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5.3057-3063; International Patent Application No. WO94/17810, published Aug. 18, 1994; International Patent Application No. WO94/23744, published Oct. 27, 1994). Examples of non-viral vectors include, but are not limited to, liposomes, polyamine derivatives of DNA, and the like.

Probes are substantially purified oligonucleotides that will hybridize under stringent conditions to at least optimally 12, 25, 50, 100, 150, 200, 250, 300, 350 or 400 consecutive sense strand nucleotide sequence; or an anti-sense strand nucleotide sequence; or of a naturally occurring mutant of the Nato3 DNA sequence of interest.

The full- or partial length native sequence Nato3 DNA may be used to "pull out" similar (homologous) sequences (Ausubel et al., supra; Sambrook, supra), such as: (1) full-length or fragments of Nato3 cDNA from a cDNA library from any species (e.g. human, murine, feline, canine, bacterial, viral, retroviral, yeast), (2) from cells or tissues, (3) variants within a species, and (4) homologues and variants from other species. To find related sequences that may encode related genes, the probe may be designed to encode unique sequences or degenerate sequences.

Sequences may also be genomic sequences including promoters, enhancer elements and introns of native Nato3 sequence.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

As used herein, a "homolog" means a protein in a group of proteins that perform the same biological function, e.g. proteins that belong to the same Pfam protein family and that provide a common enhanced trait in various organisms of this invention. Homologs are expressed by homologous genes. With reference to homologous genes, homologs include orthologs, e.g., genes expressed in different species that evolved from a common ancestral genes by specification and encode proteins retain the same function, but do not include paralogs, e.g., genes that are related by duplication but have evolved to encode proteins with different functions. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. When optimally aligned, homolog proteins have typically at least about 60% identity, in some instances at least about 70%, for example about 80% and even at least about 90% identity over the full length of a protein identified as being associated with imparting an enhanced trait when expressed in mammalian cells. In one aspect of the invention homolog proteins have an amino acid sequence that has at least 90% identity to a consensus amino acid sequence of proteins and homologs disclosed herein. A "homologous nucleic acid sequence" or "homologous amino acid sequence," or variations thereof, refer to sequences characterized by a homology at the nucleotide level or amino acid level. Homologous nucleotide sequences encode those sequences coding for isoforms of Nato3. Isoforms may be expressed in different tissues of the same organism as a result of, for example, alternative splicing of RNA. Alternatively, different genes may encode isoforms. In the invention, homologous nucleotide sequences include nucleotide sequences encoding for a mutant Nato3 polypeptide of species other than humans, including, but not limited to vertebrates, and thus may include, e.g., frog, mouse, rat, rabbit, dog, cat cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding a human Nato3. Homologous nucleic acid sequences include those nucleic acid sequences that encode conservative amino acid substitutions in a Nato3 sequence of interest, as well as a polypeptide possessing Nato3 biological activity.

"Percent (%) nucleic acid sequence identity" with respect to a Nato3 wild-type or mutant polynucleotide sequence is defined as the percentage of nucleotides in a candidate sequence that are identical with the nucleotides in that particular Nato3 wild-type or mutant polynucleotide sequence, after aligning the sequences and introducing gaps, if necessary, to achieve the maximum percent sequence identity.

Alignment for purposes of determining % nucleic acid sequence identity may be achieved in various ways that are within the skill in the art for instance, using publicly available computer software such as BLAST, BLAST-2, ALIGN, Megalign (DNASTAR) or ClustalX software. Those skilled in the art may determine appropriate parameters for measuring alignment, including any algorithms needed to achieve maximal alignment over the full length of the sequences being compared. BLAST protein searches may be performed with the XBLAST program (designated "blastn" at the NCBI web site) or the NCBI "blastp" program, using the following parameters: expectation value 10.0, BLOSUM 62 scoring matrix to obtain amino acid sequences homologous to a protein molecule described herein.

To obtain gapped alignments for comparison purposes, Gapped BLAST may be utilized as described in Altschul et al. (1997, Nucleic Acids Res. 25: 3389-3402). Alternatively, PSI-Blast or PHI-Blast may be used to perform an iterated search which detects distant relationships between molecules and relationships between molecules which share a common pattern. When utilizing BLAST, Gapped BLAST, PSI-Blast, and PHI-Blast programs, the default parameters of the respective programs (e.g., XBLAST and NBLAST) may be used.

The "open reading frame" (ORF) of a Nato3 gene encodes Nato3. An ORF is a nucleotide sequence that has commonly a start codon (ATG) and terminates commonly with one of the three "stop" codons (TAA, TAG, or TGA). In this invention, however, an ORF may be any part of a coding sequence that may or may not comprise a start codon and a stop codon. To achieve a unique sequence, preferable Nato3-ORFs encode at least 50 amino acids.

"Recombinant polynucleotide" refers to a polynucleotide having sequences that are not naturally joined together. An amplified or assembled recombinant polynucleotide may be included in a suitable vector, and the vector may be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

The various amino acids of the various polypeptides described herein are illustrated using their single letter amino acid designation. Similarly, substitutions of wild type amino acids are illustrated as substitutions of single letter abbreviations. For example, the amino acid substitution T132E of Nato3 mutant polypeptide denotes that threonine (T) at position 132 of wild type mouse Nato3 as set forth in SEQ ID NO:2 is substituted with glutamic acid (E).

The term "polypeptide" refers to a polymer composed of amino acid residues, related naturally occurring structural variants, and synthetic nonnaturally occurring analogs thereof linked via peptide bonds, related naturally occurring structural variants, and synthetic non-naturally occurring analogs thereof. Synthetic polypeptides may be synthesized, for example, using an automated polypeptide synthesizer.

By "tag" polypeptide is meant any protein which, when linked by a peptide bond to a protein of interest, may be used to localize the protein, to purify it from a cell extract, to immobilize it for use in binding assays, or to otherwise study its biological properties and/or function. A chimeric (i.e., fusion) protein containing a "tag" epitope may be immobilized on a resin which binds the tag. Such tag epitopes and resins which specifically bind them are well known in the art and include, for example, tag epitopes comprising a plurality of sequential histidine residues (His6), which allows isolation of a chimeric protein comprising such an epitope on nickel-nitrilotriacetic acid-agarose, a hemagglutinin (HA) tag epitope allowing a chimeric protein comprising such an epitope to bind with an anti-HA-monoclonal antibody affinity matrix, a myc tag epitope allowing a chimeric protein comprising such an epitope to bind with an antimyc-monoclonal antibody affinity matrix, a glutathione-S-transferase tag epitope, and a maltose binding protein (MBP) tag epitope, which may induce binding between a protein comprising such an epitope and a glutathione- or maltose Sepharose column, respectively. Production of proteins comprising such tag epitopes is well known in the art and is described in standard treatises such as Sambrook et al., supra, and Ausubel et al., supra. Likewise, antibodies to the tag epitope allow detection and localization of the fusion protein in, for example, Western blots, ELISA assays, and immunostaining of cells.

"Mammal" for purposes of treatment refers to any animal classified as a mammal, including humans, domestic and farm animals, and zoo, sports, or pet animals, such as dogs, horses, cats, cows, etc. Preferably, the mammal is human.

"Physiologically acceptable" carriers, excipients, or stabilizers are ones which are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

"A polypeptide having biological activity" refers to a polypeptide exhibiting activity similar to, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention).

"Treatment" refers to both therapeutic treatment and prophylactic or preventative measures. Those in need of treatment include those already with the disorder as well as those in which the disorder is to be prevented.

The term "subject" generally refers to any living organism to which compounds described herein are administered and may include, but is not limited to, any human, primate, or non-human mammal, for example, an experimental animal or model, such as a mouse, rat, rabbit, guinea pig, hamster, ferret, dog, cat, and the like. In some embodiments, a subject may also include non-mammalian animals, or non-vertebrate animals. A "subject" may or may not be exhibiting the signs, symptoms, or pathology of aberrant angiogenesis at any stage of any embodiment.

The term "purified" as applied to a Nato3 mutant polypeptide as used herein, refers to a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated.

As used herein, the terms "administration" or "administering" refers to the act of giving a Nato3 mutant polynucleotide or a cell transformed or transfected Nato3 mutant polynucleotide as part of a therapeutic treatment (e.g., compositions of the present invention) to a subject (e.g., a subject or in vivo, in vitro, or ex vivo cells, tissues, and organs). Exemplary routes of administration to the human body may be through the eyes (ophthalmic), mouth (oral), skin (transdermal), nose (nasal), lungs (inhalant), oral mucosa (buccal), ear, by injection (e.g., intravenously, subcutaneously, intramuscularly, intracranially, intratumorally, intraperitoneally, etc.) and the like.

As used herein, the term "co-administration" refers to the administration of at least two agent(s) (e.g., a Nato3 mutant polypeptide and one or more other agents such as an anti-inflammatory agent, or dopamine or an analog thereof) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration may be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

As used herein, the term "toxic" refers to any detrimental or harmful effects on a subject, a cell, or a tissue as compared to the same cell or tissue prior to the administration of the toxicant.

As used herein, the term "pharmaceutical composition" refers to the combination of an active agent (e.g., a Nato3 mutant polypeptide) with a carrier, inert or active, making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintegrants (e.g., potato starch or sodium starch glycolate), and the like. The compositions also may include stabilizers and preservatives. For examples of carriers, stabilizers and adjuvants. (See e.g., Martin, Remington's Pharmaceutical Sciences, 15th Ed., Mack Publ. Co., Easton, Pa. (1975), incorporated herein by reference).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as whole blood, plasma, serum and the like, and other fluids typically found within or produced by an organism, such as cerebrospinal fluid, ascites fluid, vitreous fluid and the like.

A. NATO3 MUTANT POLYPEPTIDES

In various embodiments of the present invention, the inventors have isolated mutant Nato3 polypeptides having at least one mutation in any one or more serine, threonine and tyrosine residues of a wild-type Nato3 protein.

A "native amino acid sequence or wild-type amino acid sequence of Nato3" comprises a polypeptide having the same amino acid sequence as the corresponding Nato3 polypeptide derived from nature. In one embodiment, a native or wild-type Nato3 polypeptide comprises the amino acid sequence of human Nato3 referenced in the National Center for Biotechnology Information (NCBI) Accession No. NP_690862 version NP_690862.1 GI:23097242 (SEQ ID NO:1 see Table 1).

TABLE 1

Amino acid and polynucleotide sequences of various wild-type and mutant Nato3 polypeptides and polynucleotides in mammals, avians and insects.

| Nato3 Species | SEQ ID NO: | Amino Acid Sequence | | | |
|---|---|---|---|---|---|
| Human | 1 | MAAYPESCVD | TTVLDFVADL | SLASPRRPLL | CDFAPGVSLG DPALALREGR |
|  |  | PRRMARFEEG | DPEEEECEVD | QGDGEEEEEE | ERGRGVSLLG RPKRKRVITY |
|  |  | AQRQAANIRE | RKRMFNLNEA | FDQLRRKVPT | FAYEKRLSRI ETLRLAIVYI |
|  |  | SFMTELLESC | EKKESG |  |  |
| Mouse | 2 | MAAYPESCLD | ATVLNFVADL | SLASPRHPLL | CEFPPGVPFG DRTLGYREGR |
|  |  | PGRLSQFDER | YQEVEGDEVE | YEDPEEEEEE | GEGRGRVASL LGRPKRKRVI |
|  |  | TYAQRQAANI | RERKRMFNLN | EAFDQLRRKV | PTFAYEKRLS RIETLRLAIV |
|  |  | YISFMTELLQ | SKEEKEAS |  |  |

TABLE 1-continued

Amino acid and polynucleotide sequences of various wild-type and mutant Nato3 polypeptides and polynucleotides in mammals, avians and insects.

| Nato3 Species | SEQ ID NO: | Amino Acid Sequence |
|---|---|---|
| Rat | 3 | MAAYPESCLD ANVLNFVADL SLASPRHPFL CEFPPGVPFE DQTLGFREGR<br>GLLQFEGRYQ EVEGGEVDYE DPEEEEEGE GRGRVASLLG RPKRKRVITY<br>AQRQAANIRE RKRMFNLNEA FDQLRRKVPT FAYEKRLSRI ETLRLAIVYI<br>SFMTELLQSK EEKEAS |
| Chicken | 4 | MSAGLFPAHR RPELLRGTAP PLPCPERLLG ASVLGFVADI SLGAPQSSSR<br>AGPSLGLTSE PPFGDRTLSL REGMARGLPL AAFGDGDLED EEEEEEERM<br>RSASLLDRPR RKRVITYAQR QAANIRERKR MFNLNEAFDQ LRKKVPTFAY<br>EKRLSRIETL RLAIVYISFM TELLNGCSRQ EAS |
| *Drosophila* | 5 | MQHPHPIDQP TYMPDVPFQP LWGQEAPPPP IVPYQELIAG FPCTDLSLWQ<br>RSQVTPLVPQ RPSTNGRANG SSSSSKKTRR RVASMAQRRA ANIRERRRMF<br>NLNEAFDKLR RKVPTFAYEK RLSRIETLRL AITYIGFMAE LLSGTPSNSH<br>KSRSDVYGSM NGHHQAPPPA IHPHHLHPAA AYQRDFASPY NHSLS |
| T101E mouse | 6 | ATGGCCGCCTATCCAGAGAGCTGCTTGGATGCTACCGTGCTGAACTTCGTAGCAGATCTCT<br>CTCTGGCCTCTCCCAGACACCCTCTTCTCTGCGAGTTCCCACCTGGGGTCCCTTTTGGGGA<br>CCGAACACTGGGGTACAGAGAGGGAAGACCTGGGAGACTGTCGCAGTTTGATGAAAGATAT<br>CAGGAAGTAGAGGGGGACGAAGTGGAATATGAGGACCCAGAAGAGGAGGAAGAGGAGGGAG<br>AGGGGCGCGGCAGAGTAGCATCCTTGCTGGGCCGCCCCAAAAGAAAAAGAGTTATTGAGTA<br>TGCCCAGCGCCAGGCCGCCAACATTCGCGAGAGGAAGAGGATGTTCAACCTAAACGAGGCC<br>TTCGACCAGCTGCGCAGAAAGGTACCCACCTTCGCTTATGAGAAGAGACTGTCGAGGATCG<br>AGACCCTCCGCTTGGCCATCGTCTACATTTCCTTCATGACCGAGCTCCTGCAGAGCAAGGA<br>GGAAAAGGAGGCCAGCTGA |
| T132E mouse | 7 | ATGGCCGCCTATCCAGAGAGCTGCTTGGATGCTACCGTGCTGAACTTCGTAGCAGATCTCT<br>CTCTGGCCTCTCCCAGACACCCTCTTCTCTGCGAGTTCCCACCTGGGGTCCCTTTTGGGGA<br>CCGAACACTGGGGTACAGAGAGGGAAGACCTGGGAGACTGTCGCAGTTTGATGAAAGATAT<br>CAGGAAGTAGAGGGGGACGAAGTGGAATATGAGGACCCAGAAGAGGAGGAAGAGGAGGGAG<br>AGGGGCGCGGCAGAGTAGCATCCTTGCTGGGCCGCCCCAAAAGAAAAAGAGTTATTACTTA<br>TGCCCAGCGCCAGGCCGCCAACATTCGCGAGAGGAAGAGGATGTTCAACCTAAACGAGGCC<br>TTCGACCAGCTGCGCAGAAAGGTACCCGAATTCGCTTATGAGAAGAGACTGTCGAGGATCG<br>AGACCCTCCGCTTGGCCATCGTCTACATTTCCTTCATGACCGAGCTCCTGCAGAGCAAGGA<br>GGAAAAGGAGGCCAGCTGA |
| S140D mouse | 8 | ATGGCCGCCTATCCAGAGAGCTGCTTGGATGCTACCGTGCTGAACTTCGTAGCAGATCTCT<br>CTCTGGCCTCTCCCAGACACCCTCTTCTCTGCGAGTTCCCACCTGGGGTCCCTTTTGGGGA<br>CCGAACACTGGGGTACAGAGAGGGAAGACCTGGGAGACTGTCGCAGTTTGATGAAAGATAT<br>CAGGAAGTAGAGGGGGACGAAGTGGAATATGAGGACCCAGAAGAGGAGGAAGAGGAGGGAG<br>AGGGGCGCGGCAGAGTAGCATCCTTGCTGGGCCGCCCCAAAAGAAAAAGAGTTATTACTTA<br>TGCCCAGCGCCAGGCCGCCAACATTCGCGAGAGGAAGAGGATGTTCAACCTAAACGAGGCC<br>TTCGACCAGCTGCGCAGAAAGGTACCCACCTTCGCTTATGAGAAGAGACTGGACAGGATCG<br>AGACCCTCCGCTTGGCCATCGTCTACATTTCCTTCATGACCGAGCTCCTGCAGAGCAAGGA<br>GGAAAAGGAGGCCAGCTGA |
| T99E Human | 9 | ATGGCGGCCTATCCGGAGAGCTGCGTGGACACTACGGTGCTGGACTTCGTCGCAGACCTGT<br>CCCTGGCCTCCCCGAGACGCCCTCTCCTCTGCGACTTCGCACCCGGGGTCTCCTTGGGGA<br>CCCAGCCCTTGCGCTCCGAGAGGGAAGACCCAGGAGGATGGCGCGGTTTGAAGAGGGGGAC<br>CCAGAAGAAGAGGAGTGCGAAGTGGACCAGGGGGACGGAGAAGAGGAGGAGGAAGAGGAGC<br>GCGGAAGAGGTGTCTCCCTATTAGGCCGCCCCAAGAGGAAAAGGTGATCGAGTACGCCCA<br>GCGCCAGGCCGCCAACATCCGCGAAAGGAAGCGGATGTTCAACCTCAACGAGGCCTTTGAC<br>CAGCTGCGGAGGAAGGTGCCCACGTTTGCTTACGAGAAAAGGCTGTCCCGGATCGAGACCC<br>TCCGCCTGGCCATCGTCTATATCTCCTTCATGACCGAGCTCTTGGAGAGCTGTGAGAAGAA<br>GGAAAGCGGCTGA |
| T130E Human | 10 | ATGGCGGCCTATCCGGAGAGCTGCGTGGACACTACGGTGCTGGACTTCGTCGCAGACCTGT<br>CCCTGGCCTCCCCGAGACGCCCTCTCCTCTGCGACTTCGCACCCGGGGTCTCCTTGGGGA<br>CCCAGCCCTTGCGCTCCGAGAGGGAAGACCCAGGAGGATGGCGCGGTTTGAAGAGGGGGAC<br>CCAGAAGAAGAGGAGTGCGAAGTGGACCAGGGGGACGGAGAAGAGGAGGAGGAAGAGGAGC<br>GCGGAAGAGGTGTCTCCCTATTAGGCCGCCCCAAGAGGAAAAGGGTGATCACCTACGCCCA<br>GCGCCAGGCCGCCAACATCCGCGAAAGGAAGCGGATGTTCAACCTCAACGAGGCCTTTGAC<br>CAGCTGCGGAGGAAGGTGCCCGAGTTTGCTTACGAGAAAAGGCTGTCCCGGATCGAGACCC<br>TCCGCCTGGCCATCGTCTATATCTCCTTCATGACCGAGCTCTTGGAGAGCTGTGAGAAGAA<br>GGAAAGCGGCTGA |
| S138D Human | 11 | ATGGCGGCCTATCCGGAGAGCTGCGTGGACACTACGGTGCTGGACTTCGTCGCAGACCTGT<br>CCCTGGCCTCCCCGAGACGCCCTCTCCTCTGCGACTTCGCACCCGGGGTCTCCTTGGGGA<br>CCCAGCCCTTGCGCTCCGAGAGGGAAGACCCAGGAGGATGGCGCGGTTTGAAGAGGGGGAC<br>CCAGAAGAAGAGGAGTGCGAAGTGGACCAGGGGGACGGAGAAGAGGAGGAGGAAGAGGAGC<br>GCGGAAGAGGTGTCTCCCTATTAGGCCGCCCCAAGAGGAAAAGGGTGATCACCTACGCCCA<br>GCGCCAGGCCGCCAACATCCGCGAAAGGAAGCGGATGTTCAACCTCAACGAGGCCTTTGAC<br>CAGCTGCGGAGGAAGGTGCCCACGTTTGCTTACGAGAAAAGGCTGGACCGGATCGAGACCC |

TABLE 1-continued

Amino acid and polynucleotide sequences of various wild-type and mutant Nato3 polypeptides and polynucleotides in mammals, avians and insects.

| Nato3 Species | SEQ ID NO: | Amino Acid Sequence |
|---|---|---|
| | | TCCGCCTGGCCATCGTCTATATCTCCTTCATGACCGAGCTCTTGGAGAGCTGTGAGAAGAA GGAAAGCGGCTGA |
| T101E mouse | 12 | MAAYPESCLD ATVLNFVADL SLASPRHPLL CEFPPGVPFG DRTLGYREGR PGRLSQFDER YQEVEGDEVE YEDPEEEEEE GEGRGRVASL LGRPKRKRVI EYAQRQAANI RERKRMFNLN EAFDQLRRKV PTFAYEKRLS RIETLRLAIV YISFMTELLQ SKEEKEAS |
| T132E mouse | 13 | MAAYPESCLD ATVLNFVADL SLASPRHPLL CEFPPGVPFG DRTLGYREGR PGRLSQFDER YQEVEGDEVE YEDPEEEEEE GEGRGRVASL LGRPKRKRVI TYAQRQAANI RERKRMFNLN EAFDQLRRKV PEFAYEKRLS RIETLRLAIV YISFMTELLQ SKEEKEAS |
| S140D mouse | 14 | MAAYPESCLD ATVLNFVADL SLASPRHPLL CEFPPGVPFG DRTLGYREGR PGRLSQFDER YQEVEGDEVE YEDPEEEEEE GEGRGRVASL LGRPKRKRVI TYAQRQAANI RERKRMFNLN EAFDQLRRKV PTFAYEKRLD RIETLRLAIV YISFMTELLQ SKEEKEAS |
| T99E Human | 15 | MAAYPESCVD TTVLDFVADL SLASPRRPLL CDFAPGVSLG DPALALREGR PRRMARFEEG DPEEEECEVD QGDGEEEEEE ERGRGVSLLG RPKRKRVIEY AQRQAANIRE RKRMFNLNEA FDQLRRKVPT FAYEKRLSRI ETLRLAIVYI SFMTELLESC EKKESG |
| T130E Human | 16 | MAAYPESCVD TTVLDFVADL SLASPRRPLL CDFAPGVSLG DPALALREGR PRRMARFEEG DPEEEECEVD QGDGEEEEEE ERGRGVSLLG RPKRKRVITY AQRQAANIRE RKRMFNLNEA FDQLRRKVPE FAYEKRLSRI ETLRLAIVYI SFMTELLESC EKKESG |
| S138D Human | 17 | MAAYPESCVD TTVLDFVADL SLASPRRPLL CDFAPGVSLG DPALALREGR PRRMARFEEG DPEEEECEVD QGDGEEEEEE ERGRGVSLLG RPKRKRVITY AQRQAANIRE RKRMFNLNEA FDQLRRKVPT FAYEKRLDRI ETLRLAIVYI SFMTELLESC EKKESG |
| T101E/ T132E mouse | 22 | MAAYPESCLD ATVLNFVADL SLASPRHPLL CEFPPGVPFG DRTLGYREGR PGRLSQFDER YQEVEGDEVE YEDPEEEEEE GEGRGRVASL LGRPKRKRVI EYAQRQAANI RERKRMFNLN EAFDQLRRKV PEFAYEKRLS RIETLRLAIV YISFMTELLQ SKEEKEAS |
| T101/ S140D mouse | 23 | MAAYPESCLD ATVLNFVADL SLASPRHPLL CEFPPGVPFG DRTLGYREGR PGRLSQFDER YQEVEGDEVE YEDPEEEEEE GEGRGRVASL LGRPKRKRVI EYAQRQAANI RERKRMFNLN EAFDQLRRKV PTFAYEKRLD RIETLRLAIV YISFMTELLQ SKEEKEAS |
| T101E/ T132E/ S140D mouse | 24 | MAAYPESCLD ATVLNFVADL SLASPRHPLL CEFPPGVPFG DRTLGYREGR PGRLSQFDER YQEVEGDEVE YEDPEEEEEE GEGRGRVASL LGRPKRKRVI EYAQRQAANI RERKRMFNLN EAFDQLRRKV PEFAYEKRLD RIETLRLAIV YISFMTELLQ SKEEKEAS |
| T99E/ T130E Human | 25 | MAAYPESCVD TTVLDFVADL SLASPRRPLL CDFAPGVSLG DPALALREGR PRRMARFEEG DPEEEECEVD QGDGEEEEEE ERGRGVSLLG RPKRKRVIEY AQRQAANIRE RKRMFNLNEA FDQLRRKVPE FAYEKRLSRI ETLRLAIVYI SFMTELLESC EKKESG |
| T99E/ S138D Human | 26 | MAAYPESCVD TTVLDFVADL SLASPRRPLL CDFAPGVSLG DPALALREGR PRRMARFEEG DPEEEECEVD QGDGEEEEEE ERGRGVSLLG RPKRKRVIEY AQRQAANIRE RKRMFNLNEA FDQLRRKVPT FAYEKRLDRI ETLRLAIVYI SFMTELLESC EKKESG |
| T99E/ T132E/ S138D | 27 | MAAYPESCVD TTVLDFVADL SLASPRRPLL CDFAPGVSLG DPALAIREGR PRRMARFEEG DPEEEECEVD QGDGEEEEEE ERGRGVSLLG RPKRKRVIEY AQRQAANIRE RKRMFNLNEA FDQLRRKVPE FAYEKRLDRI ETLRLAIVYI SFMTELLESC EKKESG |

A "Nato3 mutant polypeptide", means a native Nato3 polypeptide or fragment thereof, having at least one amino acid substitution of a threonine, tyrosine or serine amino acid of a native or wild-type Nato3 amino acid sequence, or fragment thereof.

Exemplary Nato3 mutant polypeptides may include a native Nato3 polypeptide or fragment thereof, having at least one amino acid substitution of a threonine, tyrosine or serine amino acid in the helix-loop-helix (HLH) domain or structural motif, of the native Nato3 amino acid sequence.

The HLH domain of Nato3 is also referred to as the Helix-loop-helix DNA-binding domain, or the helix loop helix domain and is described further in accession numbers cd00083, pfam0010, and smart00353 and are readily identifiable using the ncbi website.

In some embodiments, isolated Nato3 mutant polypeptides of the present invention have an amino acid sequence that contains one or more amino acid substitutions at the substituted positions indicated by a serine, threonine and tyrosine residue in the Nato3 protein members of SEQ ID NO: 1-5 as shown in Table 1. In some embodiments, the mutation of one or more serine, threonine or tyrosine amino acid residues includes at least one mutation of a serine, threonine or tyrosine amino acid residue in the region of Nato3 that spans amino acids 99 to 158, for example, the region or span of amino acids 99 to 158 in the human Nato3 wild-type sequence of SEQ ID NO: 1. This region of Nato3 polypeptides is called the helix-loop-helix (HLH) domain or structural motif, and is fairly well conserved among many species. Members of the HLH superfamily have two highly conserved and functionally distinct domains, which together make up a region of approximately 60 amino-acid residues. At the amino-terminal end of this region is the basic domain, which binds the transcription factor to DNA at a consensus hexanucleotide sequence known as the E box. Different families of HLH proteins recognize different E-box consensus sequences. At the carboxy-terminal end of the region is the HLH domain, which facilitates interactions with other protein subunits to form homo- and hetero-dimeric complexes. Many different combinations of dimeric structures are possible, each with different binding affinities between monomers. The heterogeneity in the E-box sequence that is recognized and the dimers formed by different HLH proteins determines how they control diverse developmental functions through transcriptional regulation A DNA-binding basic region is followed by two alpha-helices separated by a variable loop region. The HLH domain forms homo- and heterodimers, dimerization creates a parallel, left-handed, four helix bundle; the basic region N-terminal to the first amphipathic helix mediates high-affinity DNA-binding. The HLH domain is found in specific DNA-binding proteins that act as transcription factors, such as Nato3. Examples of polypeptides, including Nato3 exemplifying the helix-loop-helix domain or structural motif spanning amino acids 99 to 158 of Nato3 are collectively grouped under the term HelixLoopHelix (HLH) conserved domain, under accession numbers cd00083, pfam0010, and smart00353 and are readily identifiable using the ncbi website.

In some embodiments, an isolated Nato3 mutant polypeptide of the present invention has an amino acid sequence that contains one or more amino acid substitutions at amino acids threonine, tyrosine and/or serine within amino acids 99-158, relative to a wild-type sequence of Nato3 as set forth in SEQ ID NOs: 1-5.

In some embodiments, an isolated Nato3 mutant polypeptide of the present invention has an amino acid sequence that contains one or more amino acid substitutions at threonine, tyrosine and/or serine residues within amino acids 99-158, relative to a wild-type sequence of Nato3 as set forth in SEQ ID NOs: 1-5. In some embodiments, an isolated Nato3 mutant polypeptide of the present invention excludes an isolated mutant Nato3 polypeptide having a mutation at position S140 wherein the serine at position 140 of SEQ ID NO:2 in mouse, is substituted with aspartic acid "D" (See SEQ ID NO: 14).

In some exemplary embodiments, an isolated Nato3 mutant polypeptide of the present invention has an amino acid sequence that contains one or more amino acid substitutions at amino acid positions 99, 100, 101, 102, 104, 116, 117, 130, 132, 133, 135, 138, 140, 142, 144, 147, 149, 150, 151, 154, 155, 156 relative to a wild-type sequence of Nato3 as set forth in SEQ ID NOs:1-5.

In some embodiments, an isolated Nato3 mutant polypeptide of the present invention has an amino acid sequence that contains one or more amino acid substitutions at amino acid positions 99, 100, 130, 133, 138, 142, 144, 149, 151, 154, relative to the wild-type sequence of Nato3 as set forth in SEQ ID NO: 1. In some embodiments, the substitution of one or more amino acids threonine, threonine and serine at positions 99, 130, and/or 138 respectively, or any combination thereof, relative to SEQ ID NO:1 may be made with any amino acid other than the wild-type amino acid at that position. In some embodiments, the substitution of one or more amino acids threonine, threonine and serine at positions 99, 130, and/or 138 respectively of the human Nato3 wild type amino acid sequence of SEQ ID NO: 1 correspond to threonine, threonine and serine at positions 101, 132, and/or 140 respectively in the mouse helix-loop-helix domain of the mouse Nato3 wild type amino acid sequence of SEQ ID NO: 2. In some illustrative embodiments, with reference to the human Nato3 wild-type sequence of SEQ ID NO:1, the threonine amino acid at position 99 may be substituted with any amino acid other than threonine. In a related embodiment, the threonine amino acid at position 99 may be substituted with a negatively charged amino acid, for example, glutamic acid or aspartic acid. In a related embodiment, with reference to the human Nato3 wild-type sequence of SEQ ID NO:1, the threonine amino acid at position 130 may be substituted with any amino acid other than threonine. For example, the threonine amino acid at position 130 may be substituted with a negatively charged amino acid, for example, glutamic acid or aspartic acid. In a related embodiment, with reference to the human Nato3 wild-type sequence of SEQ ID NO:1, the serine amino acid at position 138 may be substituted with any amino acid other than serine. For example, the serine amino acid at position 138 may be substituted with a negatively charged amino acid, for example, glutamic acid or aspartic acid. In still further embodiments, an illustrative Nato3 mutant polypeptide may include a polypeptide having one to ten amino acid substitutions at amino acid positions 99, 100, 130, 133, 138, 142, 144, 149, 151, 154, or combinations thereof, relative to the wild-type sequence of Nato3 as set forth in SEQ ID NO: 1, wherein the amino acid substitution at each or a combination of positions may be any amino acid other than the wild-type amino acid at their respective position, or an amino acid substitution at each or a combination of positions with a negatively charged amino acid, for example, glutamic acid or aspartic acid.

In some embodiments, Nato3 mutant polypeptides may include double mutants, wherein two of serine or threonine or tyrosine are mutated relative to the native sequence of Nato3. In some embodiments, Nato3 mutant polypeptides may include double mutants, wherein two of serine, threonine and tyrosine are mutated in the HLH domain of a Nato3 native sequence. In some embodiments, Nato3 mutant polypeptides may include double mutants, wherein two of serine, threonine and tyrosine are mutated in the HLH domain of a Nato3 native sequence as provided in SEQ ID NOs:1-5. In some embodiments, Nato3 mutant polypeptides may include double mutants, wherein two of serine, threonine and tyrosine are mutated in the HLH domain of a Nato3 native sequence as provided in SEQ ID NOs:1-5, for example, T101E and T132E in mouse Nato3 SEQ ID NO:2; T101E and S140D in mouse Nato3 SEQ ID NO:2; T99E and T130E in human Nato3 SEQ ID NO:1; and T99E and S138D in human Nato3 SEQ ID NO:1.

In still further embodiments, Nato3 mutant polypeptides have one or more amino acid substitution at threonine, tyrosine and serine residues within amino acids 99-158, or combinations thereof, relative to a wild-type sequence of Nato3 as set forth in SEQ ID NOs: 1-5, and may have from about one to about 25 conservative amino acid substitutions provided that at least one threonine, tyrosine and/or serine residue within amino acids 99-158, or combinations thereof, relative to a wild-type sequence of Nato3 as set forth in SEQ ID NOs: 1-5 is substituted with any amino acid other than the wild-type amino acid at that position, for example, a negatively charged amino acid, for example, glutamic acid or aspartic acid. In some embodiments, Nato3 mutant polypeptides of the present invention have at least 85%, or at least 90%, or at least 92%, or at least 93%, or at least 94%, or at least 95%, or at least 96%, or at least 97%, or at least 98%, or at least 99%, or at least 99.5% sequence identity to a wild-type Nato3 polypeptide as set forth in SEQ ID NOs: 1-5, and have one or more amino acid substitution at threonine, tyrosine and serine residues within amino acids 99-158, or combinations thereof, relative to a wild-type sequence of Nato3 as set forth in SEQ ID NOs: 1-5.

In some embodiments, the present invention provides a Nato3 mutant polypeptide having at least 85% amino acid sequence identity to SEQ ID NO:1, and having at least one threonine, tyrosine and/or serine amino acid substitution within amino acids 99-158, relative to a wild-type sequence of Nato3 as set forth in SEQ ID NO:1, wherein the replacing amino acid residue is any amino acid other than the wild-type amino acid, for example, the replacing amino acid is a negatively charged amino acid, for example, glutamic acid and/or aspartic acid.

In some embodiments, exemplary Nato3 mutant polypeptides of the present invention include polypeptides having the amino acid sequence of SEQ ID NOs: 12-17, or a polypeptide encoded by a polynucleotide as provided in SEQ ID NOs: 6-11, or a polynucleotide that hybridizes under stringent conditions to a polynucleotide of any one of SEQ ID NOs: 6-11, or a complement sequence thereof.

Conservative amino acid replacements are those that take place within a family of amino acids that are related in their side chains. Genetically encoded amino acids are may be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire may be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, WH Freeman and Co., 1981). Whether a change in the amino acid sequence of a polypeptide results in a functional Nato3 mutant polypeptide (e.g. functional in the sense that the resulting polypeptide mimics the functionality of the wild-type form) may be readily determined by assessing the ability of the Nato3 mutant polypeptide to produce a response in cells in a fashion similar to the wild-type Nato3 protein. Polypeptides in which more than one amino acid replacement has taken place may readily be tested in the same manner.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity may be achieved in various ways that are within the skill in the art, for instance, using publicly available computer software such as BLAST, BLAST-2, ALIGN or Megalign (DNASTAR) software. Those skilled in the art may determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, as described in U.S. Pat. No. 6,828,146.

The isolated Nato3 mutant polypeptides of the present technology may be synthesized chemically, or may be obtained recombinantly by expressing a nucleic acid in an expression vector, using standard and well established techniques known in the field of molecular biology. In this regard, the practice of the present technology will employ, unless otherwise indicated, conventional techniques of molecular biology, microbiology, recombinant DNA technology and immunology, which are within the skill of those working in the art. Such techniques are explained fully in the literature. Examples of particularly suitable texts for consultation include the following: Sambrook Molecular Cloning; A Laboratory Manual, Second Edition (1989); DNA Cloning, Volumes I and II (D. N Glover ed. 1985); Oligonucleotide Synthesis (M. J. Gait ed. 1984): Nucleic Acid Hybridization (B. D. Hames & S. J. Higgins eds. 1984); Transcription and Translation (B. D. Hames & S. J. Higgins eds. 1984); Animal Cell Culture (R. I. Freshney ed. 1986); Immobilized Cells and Enzymes (IRL Press, 1986); B. Perbal, A Practical Guide to Molecular Cloning (1984); the Methods in Enzymology series (Academic Press, Inc.), especially volumes 154 & 155; Gene Transfer Vectors for Mammalian Cells (J. H. Miller and M. P. Calos eds. 1987, Cold Spring Harbor Laboratory); Immunochemical Methods in Cell and Molecular Biology (Mayer and Walker, eds. 1987, Academic Press, London); Scopes, (1987) Protein Purification: Principles and Practice, Second Edition (Springer Verlag, N.Y.); and Handbook of Experimental Immunology, Volumes I-IV (D. M. Weir and C. C. Blackwell eds. 1986) which are all incorporated by reference herein in their entireties.

In various embodiments, Nato3 mutant polypeptides are recombinantly produced. Methods for producing the isolated Nato3 mutant polypeptides of the present invention may be performed using established and known recombinant methods described in the art, and as exemplified in the Examples section herein.

B. NATO3 MUTANT POLYPEPTIDE ENCODING POLYNUCLEOTIDES

In some embodiments, the present invention provides a polynucleotide that encodes a Nato3 mutant polypeptide or a complement sequence thereof. As used herein, the term "nucleic acid" refers to polynucleotides such as deoxyribonucleic acid (DNA), and, where appropriate, ribonucleic acid (RNA). The term should also be understood to include, as applicable to the embodiment being described, single-stranded (such as sense or antisense) and double-stranded polynucleotides. In various embodiments, Nato3 mutant polypeptide encoding polynucleotides (hereinafter referred to as "Nato3 mutant polynucleotides") may be combined with or cloned into larger DNA or RNA constructs. In some embodiments, Nato3 mutant polynucleotides may be cloned into plasmids, cosmids, viral genetic constructs and other expression vectors that contain control sequences that enable the stable or transient expression, and/or transfection and/or transduction of the cloned polynucleotides in one or more cell types, including prokaryotic and eukaryotic cells.

C. RECOMBINANT CONSTRUCTS AND VECTORS

In certain aspects, the present invention also provides isolated and/or recombinant nucleic acids encoding a Nato3 mutant polypeptide or a Nato3 fusion protein. The subject nucleic acids may be single-stranded or double-stranded, DNA or RNA molecules. These nucleic acids are useful as therapeutic agents. For example, these nucleic acids are useful in making recombinant Nato3 mutant polypeptides which may be administered to an embryonic, cell or an individual as therapeutics. Alternative, these nucleic acids may be directly administered to a cell or an individual as therapeutics such as in gene therapy. In certain embodiments, the invention provides isolated or recombinant nucleic acid sequences that are at least 85%, 90%, 95%, 97%, 98%, 99% or 100% identical to a region of the nucleotide sequence depicted in SEQ ID NOs:6-11 in which the polynucleotide sequence encodes a Nato3 mutant polypeptide as described herein. One of ordinary skill in the art will appreciate that nucleic acid sequences complementary to the subject nucleic acids, and variants of the subject nucleic acids are also within the scope of this invention. In further embodiments, the nucleic acid sequences of the invention may be isolated, recombinant, and/or fused with a heterologous nucleotide sequence, or in a DNA library.

In other embodiments, nucleic acids of the invention also include polynucleotide sequences that hybridize under highly stringent conditions to the polynucleotide sequence depicted in SEQ ID NO:6-11, or a complement sequence thereof. As discussed above, one of ordinary skill in the art will understand readily that appropriate stringency conditions which promote DNA hybridization may be varied. One of ordinary skill in the art will understand readily that appropriate stringency conditions which promote DNA hybridization may be varied. For example, one could perform the hybridization at 6.0× sodium chloride/sodium citrate (SSC) at about 45° C., followed by a wash of 2.0×SSC at 50° C. For example, the salt concentration in the wash step may be selected from a low stringency of about 2.0×SSC at 50° C. to a high stringency of about 0.2×SSC at 50° C. In addition, the temperature in the wash step may be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

In some embodiments, the recombinant Nato3 mutant polynucleotides or nucleic acids of the invention may be operably linked to one or more regulatory nucleotide sequences in an expression construct. Regulatory nucleotide sequences will generally be appropriate for a host cell used for expression. Numerous types of appropriate expression vectors and suitable regulatory sequences are known in the art for a variety of host cells. Typically, one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In some embodiments, the nucleotide sequence encoding a Nato3 mutant polypeptide is operably fused (in frame) to a different signal peptide other than the first 24 amino acid sequences of SEQ ID NO:1, for example, the Nato3 mutant polypeptide is fused to a tag, for example, a hexa-His peptide, Glutathione S-Transferase (GST), Green Fluorescent Protein (GFP), Enhanced Green Fluorescent Protein (e-GFP), c-myc, hemaglutinin antigen (HA), FLAG, SUMO, TAP, maltose binding protein (MBP) at the N-terminus and/or C-terminus.

In some embodiments, an exemplary Nato3 mutant polynucleotide is provided in an expression vector comprising a nucleotide sequence encoding a Nato3 mutant polypeptide and operably linked to at least one regulatory sequence. Regulatory sequences are art-recognized and are selected to direct expression of the soluble polypeptide. Accordingly, the term regulatory sequence includes promoters, enhancers, and other expression control elements. Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express DNA sequences encoding a soluble polypeptide. Such useful expression control sequences, include, for example, the early and late promoters of SV40, tet promoter, adenovirus or cytomegalovirus immediate early promoter (CMV-IE), the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., PhoS, the promoters of the yeast a-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

As used herein, the terms "transduction" and "transfection" are art recognized and mean the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a dsRNA construct. "Transient transfection" refers to cases where exogenous DNA does not integrate into the genome of a transfected cell, e.g., where episomal DNA is transcribed into mRNA and translated into protein. A cell has been "stably transfected" with a nucleic acid construct when the nucleic acid construct is capable of being inherited by daughter cells.

The present invention also pertains to a host cell transfected or transformed with a recombinant gene including a coding sequence for one or more of the subject Nato3 mutant polypeptides. The host cell may be any prokaryotic or eukaryotic cell. For example, a soluble Nato3 mutant polypeptide of the invention may be expressed in bacterial cells such as E. coli, insect cells (e.g., using a baculovirus expression system), yeast, or mammalian cells. Other suitable host cells are known to those skilled in the art. Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pETDuet™, pBSKS, pNH8A, pNH16a, pNH18A, pNH46A (Stratagene); ptrc99a, pKK223-3, pKK233-3, pDR540, pRIT5 (Pharmacia); 2) Eukaryotic—pWLNEO, pSV2CAT, pOG44, PXT1, pSG (Stratagene) pSVK3, pBPV, pMSG, pSVL (Pharmacia); and 3) Baculovirus—pPbac and pMbac (Stratagene). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements. In some embodiments of the present invention, transcription of the DNA encoding the Nato3 mutant polypeptides by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In certain embodiments of the present invention, the Nato3 mutant polynucleotide sequence in the expression vector is operatively linked to an appropriate expression control sequence(s) (for example, a promoter) to direct mRNA synthesis. Promoters useful in the present invention include, but are not limited to, the LTR or SV40 promoter, the E. coli lac or trp, the phage lambda PL and PR, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or selectable antibiotic markers, for example, tetracycline or ampicillin resistance in E. coli).

In other embodiments, the expression vector may also contain a ribosome binding site for translation initiation (IRES) and a transcription terminator. In still other embodiments of the present invention, the vector may also include appropriate sequences for amplifying expression.

In a further embodiment, the present invention provides host cells containing the above-described vector constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell may be a prokaryotic cell (e.g., a bacterial cell). Specific examples of host cells include, but are not limited to, Escherichia coli, Salmonella typhimurium, Bacillus subtilis, species within the genera Pseudomonas, Streptomyces, Staphylococcus, as well as eukaryotic host cells Saccharomyces cerevisiae, Schizosaccharomyces pombe, Drosophila S2 cells, Spodoptera Sf9 cells, Chinese hamster ovary (CHO) cells, COS-7 lines of monkey kidney fibroblasts, C127, 3T3, 293, 293T, HeLa, embryonic stem cells, induced adult pluripotent stem cells, epithelial cell lines, (for example, A549, BEAS-2B, PtK1, NCI H441), BHK cell lines, T-1 (tobacco cell culture line), root cell and cultured plant cells. The constructs in host cells may be used in a conventional manner to produce the gene product encoded by the recombinant sequence. In some embodiments, introduction of the construct into the host cell may be accomplished by calcium phosphate transfection, DEAE-Dextran mediated transfection, or electroporation, gene gun approach and other known methods for introducing DNA into cells (See e.g., Davis et al. [1986] Basic Methods in Molecular Biology). Alternatively, in some embodiments of the present invention, the polypeptides and polynucleotides of the invention may be synthetically produced by conventional peptide and oligonucleotide synthesizers.

Polypeptides and proteins may be expressed in mammalian cells, yeast, bacteria, or other cells under the control of appropriate promoters. Cell-free translation systems may also be employed to produce such proteins using RNAs derived from the DNA constructs of the present invention. Appropriate cloning and expression vectors for use with prokaryotic and eukaryotic hosts are described by Sambrook, et al. (1989) Molecular Cloning: A Laboratory Manual, Second Edition, Cold Spring Harbor, N.Y. Exemplary methods for expressing Nato3 mutant polypeptides are provided in further detail in the Examples below. Additionally cell penetrating polypeptides may be linked to the Nato3 mutant polypeptides described herein and directly introduced into the target cells by endocytosis.

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of Nato3 proteins may be disrupted by any convenient method, including freeze-thaw cycling, sonication, mechanical disruption, or use of cell lysing agents.

The Nato3 mutant polypeptide of the present invention may be expressed in insect cells using baculoviral vectors, or in mammalian cells using vaccinia virus or specialized eukaryotic expression vectors. For expression in mammalian cells, the Nato3 mutant cDNA sequence may be ligated to heterologous promoters, such as the simian virus (SV40) promoter in the pSV2 vector or other similar vectors and introduced into cultured eukaryotic cells such as COS cells to achieve transient or long-term expression. The stable integration of the Nato3 mutant polynucleotide construct may be maintained in mammalian cells by biochemical selection, such as neomycin and mycophenolic acid. The DNA sequence may be altered using procedures such as restriction enzyme digestion, fill-in with DNA polymerase, deletion by exonuclease, extension by terminal deoxynucleotide transferase, ligation of synthetic or cloned DNA sequences and site-directed sequence alteration with the use of specific oligonucleotides together with PCR.

The cDNA sequence or portions thereof may be introduced into eukaryotic expression vectors by conventional techniques. These vectors permit the transcription of the cDNA in eukaryotic cells by providing regulatory sequences that initiate and enhance the transcription of the cDNA and ensure its proper splicing and polyadenylation. The endogenous mammalian Nato3 gene promoter may also be used. Different promoters within vectors have different activities, which alters the level of expression of the cDNA. In addition, certain promoters may also modulate function such as the glucocorticoid-responsive promoter from the mouse mammary tumor virus.

Cell lines may also be produced which have integrated the vector into the genomic DNA. In this manner, the Nato3 mutant polypeptide is produced on a continuous basis. Vectors are introduced into recipient cells by various methods including calcium phosphate, strontium phosphate, electroporation, lipofection, DEAE dextran, electroporation, microinjection, or by protoplast fusion. Alternatively, the cDNA may be introduced by infection using viral vectors. Using the techniques mentioned, the expression vectors containing the Nato3 mutant polynucleotide or portions thereof may be introduced into a variety of mammalian cells from other species or into non-mammalian cells. The recombinant expression vector, according to this invention, comprises the selected DNA of the DNA sequences of this invention for expression in a suitable host. The DNA is operatively joined in the vector to an expression control sequence in the recombinant DNA molecule so that normal or mutant protein may be expressed. The expression control sequence may be selected from the group consisting of sequences that control the expression of genes of prokaryotic or eukaryotic cells and their viruses and combinations thereof. The expression control sequence may be selected from the group consisting of the lac system, the trp system, the tac system, the trc system, major operator and promoter regions of phage lambda, the control region of the fd coat protein, early and late promoters of SV40, promoters derived from polyoma, adenovirus, retrovirus, baculovirus, simian virus, 3-phosphoglycerate kinase promoter, yeast acid phosphatase promoters, yeast alpha-mating factors and combinations thereof.

The host cells to be transfected with the vectors of this invention may be from a host selected from the group consisting of yeasts, fungi, insects, mice or other animals or plant hosts or may be human tissue cells. For the mutant Nato3 DNA sequence, similar systems are employed to express and produce the Nato3 mutant polypeptides.

In various embodiments, the transformed, or transfected cells expressing a polynucleotide that encodes a Nato3 mutant polypeptide or a complementary sequence thereof may be mammalian cells. In some embodiments, the mammalian cells are stem cells derived from a mammalian source, such as a human embryonic stem cell or a human "adult" ("non-embryonic") pluripotent stem cell or any other tissue specific stem cells, for example, mesenchymal stem cells. In various embodiments, embryonic and non-embryonic stem cells may be transformed and/or transfected using established techniques, for example, microinjection, homologous recombination, electroporation, calcium-phosphate mediated transfection, liposome-mediated transfection, retroviral transfection or any other established method for stably or transiently expressing the Nato3 mutant polynucleotide. In some embodiments, mammalian cells are transduced by the direct addition of a Nato3 mutant polypeptide through the use of a cell-penetrating peptide linked to the Nato3 mutant polypeptide as described in Kim D, Kim C H, Moon J I, et al. Generation of Human Induced Pluripotent Stem Cells by Direct Delivery of Reprogramming Proteins. Cell Stem Cell. 2009; 4(6):472-476, Rhee Y H, Ko J Y, Chang M Y, et al. Protein-based human iPS cells efficiently generate functional dopamine neurons and may treat a rat model of Parkinson disease. The Journal of Clinical Investigation. 2011; 121(6):2326-2335, the disclosures of which are incorporated by reference herein in their entirety.

In some related embodiments, the present invention provides a population of genetically modified isolated population of dopaminergic neuron progenitors and/or dopaminergic neurons containing a mutant (single or double mutant) Nato3 as exemplified herein. Using the methods described above, the isolated population comprising a polynucleotide are transformed or transfected with a mutant Nato3 polynucleotide operable to encode a mutant Nato3 polypeptide. The population of dopaminergic neuron progenitors and/or dopaminergic neurons can be derived from the subject to be treated with the autologous cell population or they may be derived from an allogeneic source and suitable transformed with a polynucleotide operable to encode and express one or more mutant Nato3 polypeptides described herein. Upon transformation and expression of the mutant Nato3 polypeptide, the population of dopaminergic neuron progenitors and/or dopaminergic neurons thus transformed express at least one marker selected from Shh, Lmx1b, and Foxa2 in at least 50% of the population either prior to implantation when cultured under suitable conditions or after implantation into the subject's brain at site where the dopaminergic neuron progenitors and/or dopaminergic neurons are required or beneficial for treatment. In some embodiments, methods for successful implantation of autologous and/or allogeneic stem cells have been previously shown. For example, successful implantation of autologous stem cells in an animal model has been exemplified and described in: "Successful Function of Autologous iPSC-Derived Dopamine Neurons following Transplantation in a Non-Human Primate Model of Parkinson's Disease. Hallett P., Deleidi M., Astradsson A., et al., Cell Stem Cell (2015) 16(3):269-74; Direct generation of functional dopaminergic neurons from mouse and human fibroblasts. Calazzo M., Dell'Anno M., Dvoretskova E., et al., Nature. (2011) 476(7359):224-227, the disclosure of which is incorporated herein by reference in its entirety.

In various embodiments the mutant Nato3 polynucleotide may be introduced into living mammalian cells (e.g. brain tissue) of a living organism by means of transformation and/or transfection. Cells treated with the mutant Nato3 polynucleotide in this manner could control the expression of the mutant Nato3 polypeptide by means of various promoters, including constitutive promoters as well as inducible promoters that can control the expression of the mutant Nato3 polynucleotide, including but not limited to glucocorticoid responsive promoters, enhancer specific promoters etc. In some embodiments, Cre recombinase can be placed under the expression of tissue specific promoters such as NG2 to drive expression only in striatal interneurons. An adeno-associated virus (AAV) can have a Cre responsive element that permits the expression of the mutant Nato3 polypeptide in the striatal interneurons, thus converting glial cells into a neuron that can integrate within the living brain, as described in Torper, O., Ottosson, D R., Pereira, M et al. In Vivo Reprogramming of Striatal NG2 Glia into Functional Neurons that Integrate into Local Host Circuitry. Cell Reports. (2015) 12(3):474-481.

D. METHODS FOR STIMULATING DIFFERENTIATION OF STEM CELLS INTO PROGENITOR DOPAMINERGIC NEURONAL CELLS AND DOPAMINERGIC NEURONS

In various embodiments, the present invention provides methods for the differentiation of brain cells to dopaminergic neuron progenitors and/or dopaminergic neurons. In some embodiments, the method includes stimulating a population of brain cells to differentiate into dopaminergic neuron progenitors and/or dopaminergic neurons, and/or dopaminergic neurons by increasing phosphorylation of Nato3 in the brain cells and culturing the brain cells until a progenitor dopaminergic neuronal, or dopamine producing phenotype cell marker is expressed in the cultured brain cells and/or dopaminergic neuron progenitors and/or dopaminergic neurons. In various embodiments, increasing phosphorylation of Nato3 in the brain cells may include introducing a Nato3 mutant polypeptide encoding polynucleotide and expressing the Nato3 mutant polypeptide in the brain cells. In other embodiments, increasing phosphorylation of endogenous Nato3 in the brain cells may include expressing an endogenous or heterologous protein kinase in the brain cells that specifically phosphorylates Nato3, or increasing the activity of endogenous protein kinases that target Nato3. In various embodiments, endogenous or heterologous protein kinases in the brain cells that specifically phosphorylates Nato3, or increasing the activity of endogenous protein kinases that target Nato3 may include cAMP dependent protein kinase (activated with 8Br-cAMP), Protein kinase B (AKT) (activated with SC79 (2-Amino-6-chloro-α-cyano-3-(ethoxycarbonyl)-4H-1-benzopyran-4-acetic acid ethyl ester), Protein kinase C (activated with 1,2-Dioctanoyl-sn-glycerol), Protein kinase G (activated with 8Br-cGMP), CAM kinase II (activated with oleic acid), and CAM kinase. In various embodiments, methods for increasing the phosphorylation of Nato3 in brain cells may include transduction and/or transfection of a polynucleotide encoding cAMP dependent protein kinase. Protein kinase B (AKT), Protein kinase C, Protein Kinase G, and/or CAM kinase II into a mammalian brain cell, for example, a human brain cell in vivo, or ex vivo as provided herein.

As used herein, a "phosphorylatable" amino acid in the sequence of Nato3 is meant to describe an amino acid within the HLH region of a Nato3 polypeptide (e.g. in the region of Nato3 that spans amino acids 99 to 158, for example, the region or span of amino acids 99 to 158 in the human Nato3 wild-type sequence of SEQ ID NO: 1 that is amenable to be phosphorylated by a protein kinase as described above, e.g. a protein kinase that can bind to and phosphorylate Nato3 in the HLH region. In some embodiments, phosphorylatable amino acids in the HLH region of Nato3 polypeptides of SEQ ID NOs:1-5 may include: tyrosine, threonine and serine among others.

As used herein, the term "brain cells" may include any cell in the nervous system, including, terminally differentiated neurons, glia, neuroblasts, and brain stem cells each having the capability to differentiate or be programmed to become dopaminergic progenitor neuronal cells and/or dopaminergic neuronal cells, Brain cells may also include neural progenitor stem cells capable of being differentiated into dopaminergic progenitor neuronal cells and dopaminergic neurons. Methods for direct lineage reprogramming of post-mitotic callosal neurons into corticofugal neurons in vivo are known in the art, for example, as provided in Rouaux, C. & Arlotta, P., Nature Cell Biology 15, 214-221 (2013) published online 26 Nov. 2012, the disclosure of which is hereby incorporated by reference in its entirety.

As used herein, the term "stem cells" have their common scientific meaning and may include omnipotent, pluripotent, multipotent stem cells. In some embodiments, stem cells may include embryonic stem cells, induced pluripotent stem cells, mesenchymal stem cells, and other tissue stem cells.

The phrase "embryonic stem cells" refers to embryonic cells which are capable of differentiating into cells of all three embryonic germ layers (i.e., endoderm, ectoderm and mesoderm), or remaining in an undifferentiated state. The phrase "embryonic stem cells" may comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrulation stage blastocyst and embryonic germ (EG) cells which are obtained from the genital tissue of a fetus any time during gestation, preferably before 10 weeks of gestation.

In some embodiments the term "induced pluripotent stem cells" (iPS; embryonic-like stem cells), refers to cells obtained by de-differentiation of adult somatic cells which are endowed with pluripotency (i.e., being capable of differentiating into the three embryonic germ cell layers, i.e., endoderm, ectoderm and mesoderm). According to some embodiments of the invention, such cells are obtained from a differentiated tissue (e.g., a somatic tissue such as skin) and undergo de-differentiation by genetic manipulation which re-program the cell to acquire embryonic stem cells characteristics. According to some embodiments of the invention, the induced pluripotent stem cells are formed by inducing the expression of Oct-4, Sox2, Kfl4 and c-Myc in a somatic stem cell. Other methods for producing iPS cells are described, for example, in Takahashi et al. (Cell, 131: 861-872, 2007) and Nakagawa et al. (Nat. Biotechnol., 26:101-106, 2008). The iPS cells are capable of self-renewal and subsequent differentiation into more than one specialized cell type or cell lineage under appropriate growth conditions either in vitro or in vivo.

As used herein, the term "pluripotent stem cell" or "PS cell" refers to a cell capable of self-replication and differentiation into cells of all three germ layers (i.e., ectoderm, mesoderm, and endoderm). Pluripotent stem cells may be, but are not limited to, ESCs and artificially-produced stem cells having characteristics of ESCs but which are not derived from an embryo (e.g., pluripotent stem cells derived from neural progenitor cells and iPS cells). In vitro self-replication, under appropriate conditions, occurs for virtually indefinite period of time and the daughter cells retain the undifferentiated (pluripotent) characteristics of the parent cells.

The embryonic stem cells of some embodiments of the invention may be obtained using well-known cell-culture methods. For example, human embryonic stem cells may be isolated from human blastocysts. Human blastocysts are typically obtained from human in vivo pre-implantation embryos or from in vitro fertilized (IVF) embryos. Alternatively, a single cell human embryo may be expanded to the blastocyst stage. For the isolation of human ES cells the zona pellucida is removed from the blastocyst and the inner cell mass (ICM) is isolated by immunosurgery, in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated into fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells see Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

It will be appreciated that commercially available stem cells may also be used with various embodiments of the present invention. Human ES cells may be purchased from the NIH human embryonic stem cells registry. Non-limiting examples of commercially available embryonic stem cell lines are BG01, BG02, BG03, BG04, CY12, CY30, CY92, CY10, TE03 and TE32.

In addition, ES cells may be obtained from other species as well, including mouse (Mills and Bradley, 2001), golden hamster [Doetschman et al., 1988, Dev Biol. 127: 224-7], rat [Iannaccone et al., 1994, Dev Biol. 163: 288-92] rabbit [Giles et al. 1993, Mol Reprod Dev. 36: 130-8; Graves & Moreadith, 1993, Mol Reprod Dev. 1993, 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci USA. 92: 7844-8; Thomson et al., 1996, Biol Reprod. 55: 254-9].

Induced pluripotent stem cells (iPS) (embryonic-like stem cells) may be generated from somatic cells by genetic manipulation of somatic cells, e.g., by retroviral transduction of somatic cells such as fibroblasts, hepatocytes, gastric epithelial cells with transcription factors such as Oct-3/4, Sox2, c-Myc, and KLF4 [Yamanaka S, Cell Stem Cell. 2007, 1(1):39-49; IH Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131: 861-872]. Other embryonic-like stem cells may be generated by nuclear transfer to oocytes, fusion with embryonic stem cells or nuclear transfer into zygotes if the recipient cells are arrested in mitosis. Additionally, embryonic-like stem cells may also be generated by using small molecule treatment, such as HDAC inhibitors and factors that act on specification of mesectodermal and endodermal specification. See for example, Huangfu, Danwei, et al. "Induction of pluripotent stem cells by defined factors is greatly improved by small-molecule compounds." Nature biotechnology 26.7 (2008): 795-797, and Shu J, Wu C, Wu Y, et al. Induction of Pluripotency in Mouse Somatic Cells with Lineage Specifiers. Cell. 2013; 153(5):963-975.

The brain cells of the present invention may be of autologous, syngeneic or allogeneic related (matched siblings or haploidentical family members) or unrelated fully mismatched source.

Culturing of neural progenitor stem cells may be performed in any media that supports neural progenitor stem cell differentiation, examples of which are described herein above.

In some embodiments, methods for differentiating brain cells into dopaminergic progenitor neuronal cells and dopamine producing neuronal cells may be achieved by introducing (either ex vivo or in vivo) using the process of transfection or transformation of these cells, at least one Nato3 mutant polynucleotide. The transfection or transformation process results in the stable or transient expression of a Nato3 mutant polypeptide in order to induce differentiation towards a dopamine producing neuron lineage.

The present invention also contemplates differentiation of brain cells including brain cells towards a dopaminergic progenitor neuronal cell and/or a dopaminergic neuronal cell phenotype by expression of a Nato3 mutant polypeptide, and/or increasing the kinase activity of one or more protein kinases in the brain cells which phosphorylate endogenous and/or exogenously expressed Nato3 polypeptide.

According to a particular embodiment, a terminally differentiated dopaminergic neuronal cell population is generated by introducing and expressing a Nato3 mutant polypeptide in a population of brain cells, for example, stem cells and/or neural progenitor cells.

As used herein, "differentiation" refers to the process whereby an unspecialized stem cell (e.g., PS cells and iPS cells) acquires phenotypic features of a specialized cell or specific cell type, e.g., a dopamine producing neural cell. Differentiation refers to the restriction of the potential of a cell to self-renew and is generally associated with a change in the functional capacity of the cell. Differentiation of a stem cell may be determined by methods well known in the art, including analysis for cell markers or morphological features associated with cells of a defined differentiated state.

As defined herein, dopaminergic neuron progenitor cells are brain cells that arise from neural stem cells in vivo are identified in the floor plate of the mesencephalon. In vivo and in culture, these cells express a combination of the following markers SHH, OTX2, FOXA2, LMX1A, LMX1B, MSX1, MSX2, EN1, EN2, ASCL1, NGN2, RALDH1 and may undergo mitosis.

As used herein, the term "dopaminergic neuron" refers to a specialized cell that at least partially adopts a neuronal morphology in culture (e.g., develops neurites) and expresses tyrosine hydroxylase (TH) and has exited the cell cycle. Optionally, the dopaminergic neuron expresses one or more of neuron-specific enolase (NSE), 1-aromatic amino acid decarboxylase, vesicular monoamine transporter 2, dopamine transporter, Nurr-1, and dopamine-2 receptor ($D_2$ Receptor).

According to still another embodiment, the cell population is generated by increasing the phosphorylation of endogenous Nato3, either by transiently or stably introducing a protein kinase that phosphorylates Nato3, or by increasing the activity of one or more protein kinases intracellularly that results in the increased phosphorylation of endogenous Nato3.

As used herein, "neural stem cells" refers to a subset of pluripotent cells which have partially differentiated along a neural cell pathway and express some neural markers including, for example, nestin. Neural stem cells may differentiate into neurons or glial cells (e.g., astrocytes and oligodendrocytes). Neural stem cells include neural progenitor cells and may be used interchangeably.

As used herein, "neural progenitor cells" refer to cultured cells derived from pluripotent stem cells (e.g., ES cells and iPS cells) which express FOXA2 and low levels of ß-tubulin, but not tyrosine hydroxylase (i.e., having a $FOXA_2^+/ß\text{-tubulin}^{LO/TH-}$ phenotype). These neural progenitor cells have the capacity to differentiate into a variety of neuronal subtypes; particularly a variety of dopaminergic neuronal subtypes.

E. METHODS FOR TREATING A NEURODEGENERATIVE DISEASE LACKING IN EXPRESSION OF DOPAMINE

In some embodiments, the present invention provides dopaminergic progenitor neuronal cells and neuronal cells that are matured and terminally differentiated expressing dopamine. In various embodiments of the present invention, the dopaminergic progenitor neuronal cells and neuronal cells have been generated by ex vivo differentiation of brain cells after stable or transient transfection or transformation of the brain cells with a polynucleotide operable to encode and express a Nato3 mutant polypeptide as described herein or a protein kinase that specifically phosphorylates Nato3 endogenously in said population of brain cells.

The dopaminergic progenitor neuronal cells and dopaminergic neuronal cells of the present invention may be useful for a variety of therapeutic purposes. Representative examples of CNS diseases or disorders that may be beneficially treated with the cells described herein include, but are not limited to, a pain disorder, a motion disorder, a dissociative disorder, a mood disorder, an affective disorder, a neurodegenerative disease or disorder, psychiatric disorders and a convulsive disorder.

Examples of such conditions include, but are not limited to, Parkinson's Disease, Amyotrophic Lateral Sclerosis (ALS), Multiple Sclerosis (MS), Huntingdon's disease (HD), autoimmune encephalomyelitis, spinal cord injury, cerebral palsy, diabetic neuropathy, glaucatomus neuropathy, macular degeneration, action tremors and tardive dyskinesia, panic, anxiety, depression, alcoholism, insomnia, manic behavior, schizophrenia, autism-spectrum disorder, manic-depressive disorders, Alzheimer's and epilepsy.

In one exemplary embodiment, the present invention provides a method for treating or preventing Parkinson's disease (PD) in a subject in need thereof. Methods for diagnosing PD are well known in the art. Therapeutic methods for treating a PD patient may include administering to the PD subject, a therapeutically effective amount of a composition comprising the mutant Nato3 polypeptide as described herein or a polynucleotide encoding the mutant Nato3 polypeptide. In some embodiments, the mutant Nato3 polypeptide may be administered in the form of a vector containing a polynucleotide sequence operable to encode a mutant Nato3 polypeptide and any other requisite regulatory elements containing promoters and other genetic elements suitable for stable and/or transient expression of a transgene containing the polynucleotide encoding a mutant Nato3 polypeptide. The vector may be delivered in ways described herein or known to those in the art. Alternatively, the subject's own stem cells, for example, tissue-specific stem cells, mesenchymal stem cells, or induced pluripotent stem cells may be transformed with polynucleotides operable to encode and express the mutant Nato3 polypeptide in the patient's own stem cells. These autologous stem cells are then reintroduced into the subject, into the basal ganglia and/or the substantia nigra for example, or other areas of the brain and/or spinal cord which then differentiate into dopaminergic progenitor neuronal cells and then into dopaminergic neurons for the treatment of PD and other neurological diseases.

In some embodiments, the use of dopaminergic progenitor neuronal cells and dopaminergic neuronal cells comprising a mutant Nato3 polypeptide, or a polynucleotide encoding a mutant Nato3 polypeptide of the present invention, is indicated for treatment of PD, action tremors and tardive dyskinesia.

The use of dopaminergic progenitor neuronal cells and dopaminergic neuronal cells of the present invention may be also indicated for treatment of traumatic lesions of the nervous system including spinal cord injury and also for treatment of stroke caused by bleeding or thrombosis or embolism because of the need to induce neurogenesis and provide survival factors to minimize insult to damaged neurons.

In any of the methods described herein, the dopaminergic progenitor neuronal cells and dopaminergic neuronal cells of the present invention may be obtained from an autologous, semi-allogeneic or non-autologous (i.e., allogeneic or xenogeneic) human donor or embryo or cord/placenta. For example, cells may be isolated from a human cadaver or a donor subject.

The cells dopaminergic progenitor neuronal cells and dopaminergic neuronal cells of the present invention of the present invention may be administered to the treated individual using a variety of transplantation approaches, the nature of which depends on the site of implantation.

The term or phrase "transplantation", "cell replacement" or "grafting" are used interchangeably herein and refer to the introduction of the dopaminergic progenitor neuronal cells and dopaminergic neuronal cells of the present invention to target tissue. As mentioned, the cells dopaminergic progenitor neuronal cells and dopaminergic neuronal cells of the present invention may be derived from the recipient or from an allogeneic, semi-allogeneic or xenogeneic donor.

The dopaminergic progenitor neuronal cells and dopaminergic neuronal cells of the present invention may be injected systemically into the circulation, administered intrathecally or grafted into the central nervous system, the spinal cord or into the ventricular cavities or subdurally onto the surface of a host brain. Conditions for successful transplantation include: (i) viability of the implant; (ii) retention of the graft at the site of transplantation; and (iii) minimum amount of pathological reaction at the site of transplantation. Methods for transplanting various nerve tissues, for example embryonic brain tissue, into host brains have been described in: "Neural grafting in the mammalian CNS", Bjorklund and Stenevi, eds. (1985); Freed, et al., PNAS Vol. 99(4), Feb. 19, 2002; Olanow et al., 2003). These procedures include intraparenchymal transplantation, i.e. within the host brain (as compared to outside the brain or extraparenchymal transplantation) achieved by injection or deposition of tissue within the brain parenchyma at the time of transplantation.

Intraparenchymal transplantation may be performed using two approaches: (i) injection of cells into the host brain parenchyma or (ii) preparing a cavity by surgical means to expose the host brain parenchyma and then depositing the graft into the cavity. Both methods provide parenchymal deposition between the graft and host brain tissue at the time of grafting, and both facilitate anatomical integration between the graft and host brain tissue. This is of importance if it is required that the graft becomes an integral part of the host brain and survives for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the donor dopaminergic progenitor neuronal cells and dopaminergic neuronal cells of the present invention or by growing the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord. The cells may also be introduced into the putamen, nucleus basalis, hippocampus cortex, striatum, substantia nigra or caudate regions of the brain, as well as the spinal cord.

The dopaminergic progenitor neuronal cells and dopaminergic neuronal cells of the present invention may also be transplanted to a healthy region of the tissue. In some embodiments, the exact location of the damaged tissue area may be unknown and the dopaminergic progenitor neuronal cells and dopaminergic neuronal cells of the present invention may be inadvertently transplanted to a healthy region. In other cases, it may be preferable to administer the cells to a healthy region, thereby avoiding any further damage to that region. Whatever the case, following transplantation, the dopaminergic progenitor neuronal cells and dopaminergic neuronal cells of the present invention may preferably migrate to the damaged area.

For transplanting, the cell suspension is drawn up into the syringe and administered to anesthetized transplantation recipients. Multiple injections may be made using this procedure.

The cellular suspension procedure thus permits grafting of the dopaminergic progenitor neuronal cells and dopaminergic neuronal cells of the present invention to any predetermined site in the brain or spinal cord, is relatively non-traumatic, allows multiple grafting simultaneously in several different sites or the same site using the same cell suspension, and permits mixtures of dopaminergic progenitor neuronal cells and dopaminergic neuronal cells of the present invention to migrate to different anatomical regions. Preferably from approximately $1 \times 10^4$ to approximately $1 \times 10^{10}$ dopaminergic progenitor neuronal cells and/or dopaminergic neuronal cells of the present invention may be introduced per graft. Cells may be administered concomitantly to different locations such as combined administration intrathecally and intravenously to maximize the chance of targeting into affected areas.

For transplantation into cavities, which may be preferred for spinal cord grafting, tissue is removed from regions close to the external surface of the central nerve system (CNS) to form a transplantation cavity, for example as described by Stenevi et al. (Brain Res. 114:1-20, 1976), by removing bone overlying the brain and stopping bleeding with a material such a gelfoam. Suction may be used to create the cavity. The graft is then placed in the cavity. More than one transplant may be placed in the same cavity using injection of dopaminergic progenitor neuronal cells and dopaminergic neuronal cells of the present invention or solid tissue implants formed therefrom. Preferably, the site of implantation is dictated by the CNS disorder being treated.

In any of the methods described herein, the dopaminergic progenitor neuronal cells and dopaminergic neuronal cells of the present invention may be administered either per se or, preferably as a part of a pharmaceutical composition that further comprises a pharmaceutically acceptable carrier.

Techniques for formulation and administration of drugs and cellular products may be found in "Remington's Pharmaceutical Sciences," Mack Publishing Co., Easton, Pa., latest edition, which is incorporated herein by reference.

As discussed above, suitable routes of administration include direct administration into the circulation (intravenously or intra-arterial), into the spinal fluid or into the tissue or organ of interest. Thus, for example the dopaminergic progenitor neuronal cells and/or dopaminergic neuronal cells of the present invention may be administered directly into the brain.

For any preparation used in the methods of the invention, the therapeutically effective amount or dose may be estimated initially from in vitro and cell culture assays. Preferably, a dose is formulated in an animal model to achieve a desired concentration or titer. Such information may be used to more accurately determine useful doses in humans, the determination of which does not require undue experimentation, but rather using conventional techniques and procedures such as one or more clinical trials.

Toxicity and therapeutic efficacy of the implantation of dopaminergic progenitor neuronal cells and dopaminergic neuronal cells of the present invention may be determined by standard pharmaceutical procedures in vitro, in cell cultures or experimental animals. For example, animal models of demyelinating diseases include shiverer (shi/shi, MBP deleted) mouse, MD rats (PLP deficiency), Jimpy mouse (PLP mutation), dog shaking pup (PLP mutation), twitcher mouse (galactosylceramidase defect, as in human Krabbe disease), trembler mouse (PMP-22 deficiency).

The data obtained from these in vitro and cell culture assays and animal studies may be used in formulating a range of dosage for use in human. The dosage may vary depending upon the dosage form employed and the route of administration utilized. The exact formulation, route of administration and dosage may be chosen by the individual physician in view of the patient's condition, (see e.g., Fingl, et al., 1975, in "The Pharmacological Basis of Therapeutics", Ch. 1 p. 1). For example, a PD patient may be monitored symptomatically for improved motor functions indicating positive response to treatment.

For injection, the cellular components (i.e. dopaminergic progenitor neuronal cells and dopaminergic neuronal cells of the present invention) of the pharmaceutical composition may be formulated in aqueous solutions, preferably in physiologically compatible buffers such as Hank's solution, Ringer's solution, or physiological salt buffer.

The dopaminergic progenitor neuronal cells and/or dopaminergic neuronal cells of the present invention may be co-administered with therapeutic agents useful in treating neurodegenerative disorders, such as gangliosides; antibiotics, neurotransmitters, neurohormones, toxins, neurite promoting molecules; and antimetabolites and precursors of neurotransmitter molecules such as L-DOPA.

F. EXAMPLES

Example 1

Experimental Procedures

Chickens

The fertilized chicken eggs were White Leghorn and acquired from Michigan State University Poultry Farm in East Lansing, Mich. Fertilized chicken embryos are not allowed to develop past 7 days.

Tissue Preparation

Embryos were grown and harvested at multiple developmental time points. The tissue was isolated to regions of the spinal cord and the mesencephalon and sectioned. The tissue was washed in PBS, cryoprotected in 15% sucrose and mounted in Tissue Tek OCT (VWR, West Chester, Pa.). They were then frozen and sectioned at 10-micron sections. The tissue sections were cut using a Leica cryostat and mounted on glass slides. The tissue slides were stored at −20° C. and the uncut sections were stored at −80° C.

Immunohistochemistry

The sections were stained with primary antibodies against the floor plate marker gene the DA neuron marker gene Nurr1 (Santa Cruz, 1:200), and EGFP (anti-goat EGFP, Abcam, 1:200; anti-rabbit EGFP, Abcam, 1:500) in GSS (1% goat serum, 0.1% Triton 100 X, and 0.1 M sodium phosphate buffer pH 7.0) overnight at 4° C. The following day the sections were washed in phosphate buffer and stained with secondary antibodies correlating with the subtype of each primary antibody (1:1000; Nurr1 with goat anti-rabbit Cy3, Jackson Laboratories, 1:200; anti-goat EGFP with donkey anti-goat FITC, Jackson Laboratories, 1:500; anti-rabbit EGFP with goat anti-rabbit FITC, Jackson Laboratories, 1:500) and counterstained with DAPI to visualize the nuclei of individual cells. Other primary antibodies that were used: Lmx1b, Foxa2 (Developmental Studies Hybridoma Bank-DSHB), Shh (DSHB), En1 (DSHB).

Mutagenesis and Preparation of Nato3 DNA

Mutant Nato3 genes were synthesized by IDT technologies with EcoRV and BglII site engineered into the 5' and 3' flanking regions, this includes the mouse Nato3 gene mutants T101E/T132E (double mutant) and T101E/S140D (double mutant), as well as the human Nato3 gene mutant S138D Nato3. The clones were excised from the parent plasmid and subcloned into the pCIG vector (Megason and McMahon, 2002). Sequences were then verified using core facilities at GVSU's Annis Water Research Institute (AWRI), grown and harvested using Qiagen DNA high speed maxi prep kit.

In Ovo Transfection

Chick embryos between 10-14 somites (HH10-12) were electroporated using 2.5 µg of pBS (pBluescript; carrier DNA) and 0.5 µg bicistronic vector containing EGFP and the gene of interest. Pulse amplitude on a BTX amplifier was set at 24 mV for 5 pulses with 1 second between pulses. After electroporation, embryos were cooled with a small amount of phosphate buffered saline (PBS) and allowed to incubate at 37° C. for 66 hours post transfection before being harvested into PBS, washed and then fixed in 4% paraformaldehyde (Pfa) at 4° C. for 45 minutes. GFP expression was confirmed in the embryos to determine the success of transfection. Successfully transfected embryos were cryoprotected in 30% sucrose in phosphate buffer and then frozen in OCT for sectioning. Embryonic tissue was sectioned at 12 µm sections in preparation for immunofluorescence.

Example 2—Selection of Targeted Phosphoacceptor Residue and Generation of Nato3 Mutants Target sites for mutations were chosen by identifying highly conserved putative phosphoacceptor residues that were part of a consensus sequence for protein kinase. We first analyzed the mouse Nato3 sequence using multiple different computer programs that identify potential phosphoacceptor residues on the basis of their proximity to a consensus sequence of amino acids (including NetPhosK, GSK3, DIPHOS, Scansite3 and KinasePhos) (Wan et al., 2008). To add rigor to the selection process, candidate residues were inspected for 100% conservation among Nato3 species and also strong homology phosphoacceptor residues present on other bHLH family member proteins using CLUSTALW analysis.

Table 2. Amino acids T101, T132 and S140 in Nato3 are highly conserved residues that may be targets for multiple kinases as predicted in silico analysis. These residues are conserved among all of the known and predicted Nato3 homologs in human, mouse, chicken and fruitfly. PKB—Protein Kinase B, PKC—Protein Kinase C, PKG, cGMP dependent protein kinase, CAMK Calcium calmodulin dependent protein kinase, CAMKII, Calcium calmodulin dependent protein kinase II, CKII Casein kinase II.

| Amino Acid residue and position number on mouse Nato3 that may be phosphorylated | Putative kinase identified by in silico analysis that target and phosphorylate threonine and serine amino acid residues in Nato3 mutants |
| --- | --- |
| Threonine 101 (T101) | PKB, PKC, PKG |
| Threonine 132 (T132) | PKB, PKC, CAMK |
| Serine 140 (S140) | PKC, PKA, CKII, CAMKII |

Mutant Nato3 gene sequence with substitutions at the corresponding residues (T101E/T132E (double mutant), T101E/S140D (double mutant) in the mouse Nato3 gene, and S138D in the human Nato3 gene) were synthesized by Integrated DNA Technologies (IDT) and subcloned into the pCIG expression vector for in vivo expression.

Figure 3:
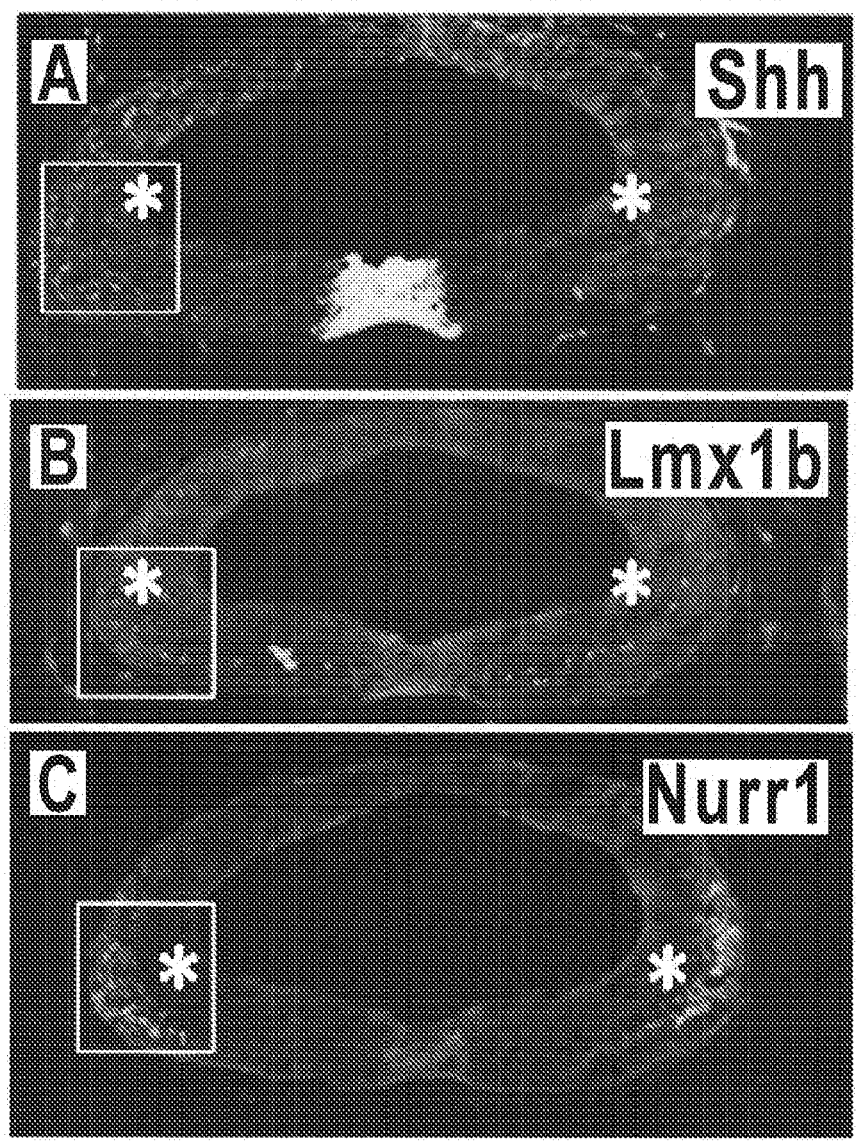
FIG. 3 depicts photomicrographs of chicken embryonic spinal cord tissue sections stained with antibodies to progenitor marker expression such as Shh, Lmx1b, and Nurr1 after the induction of expression of the T101E/T132E (double mutant) mouse Nato3 mutant polypeptide. Panel A depicts expression of Shh. Panel B depicts expression of Lmx1b and Panel C depicts expression of Nurr1.

Example 3—T101E/T132E (Double Mutant) Induces Ectopic Expression of Floor Plate Markers and Midbrain DA Neuron Progenitor Markers in the Midbrain and Spinal Cord Shh is endogenously expressed by floor plate cells and is one of the most commonly used markers to identify that cell linage in the spinal cord and the midbrain. A second commonly used marker is Foxa2, which may be expressed by floor plate cell lineage and midbrain DA progenitors. In previous studies, wild-type Nato3 could induce expression of Shh and Foxa2 in the ventral caudal midbrain in a small percentage of transfected cells. In the spinal cord, the wild-type Nato3 could not induce expression of Shh or Foxa2. When the mutant Nato3 T101E/T132E (double mutant) is overexpressed on one side of the midbrain, we find profound ectopic expression of Shh (See FIG. 3A, and FIG. 4A) and Foxa2 (data not shown) relative to the untreated side of the midbrain section.

Lmx1b expression is seen in midbrain FP cells that serve as DA neuron progenitors and DA neurons. Thus, unlike Shh, Lmx1b expression indicates that a cell has some characteristics of midbrain progenitors. Similar to the wild-type Nato3, overexpression of T101E/T132E (double mutant) Nato3 induced expression of Lmx1b in various regions of the midbrain and spinal cord, although the induction of expression of Lmx1b by T101E/T132E (double mutant) Nato3 was much more profound.

Lmx1b expression is seen in midbrain FP cells that serve as DA neuron progenitors and DA neurons. Thus, unlike Shh, Lmx1b expression indicates that a cell has some characteristics of midbrain progenitors. Similar to the wild-type Nato3, overexpression of T101E/T132E (double mutant) Nato3 induced expression of Lmx1b in various regions of the midbrain and spinal cord (Peterson et al., 2015), although the induction of expression of Lmx1b by T101E/T132E (double mutant) Nato3 was much more profound.

Nurr1 is an immature DA neuron marker and indicates a commitment to a dopamine neuron lineage and exit from the cell cycle. Unlike the markers for floor plate cells (Shh) or DA neuron progenitors (Lmx1b), there seems to be no difference in the amount or location of Nurr1 expression between the T101E/T132E (double mutant) overexpressing and untreated sides of the midbrain. Similar results were seen with the T101E Nato3 mutant (data not shown).

Figure 4:
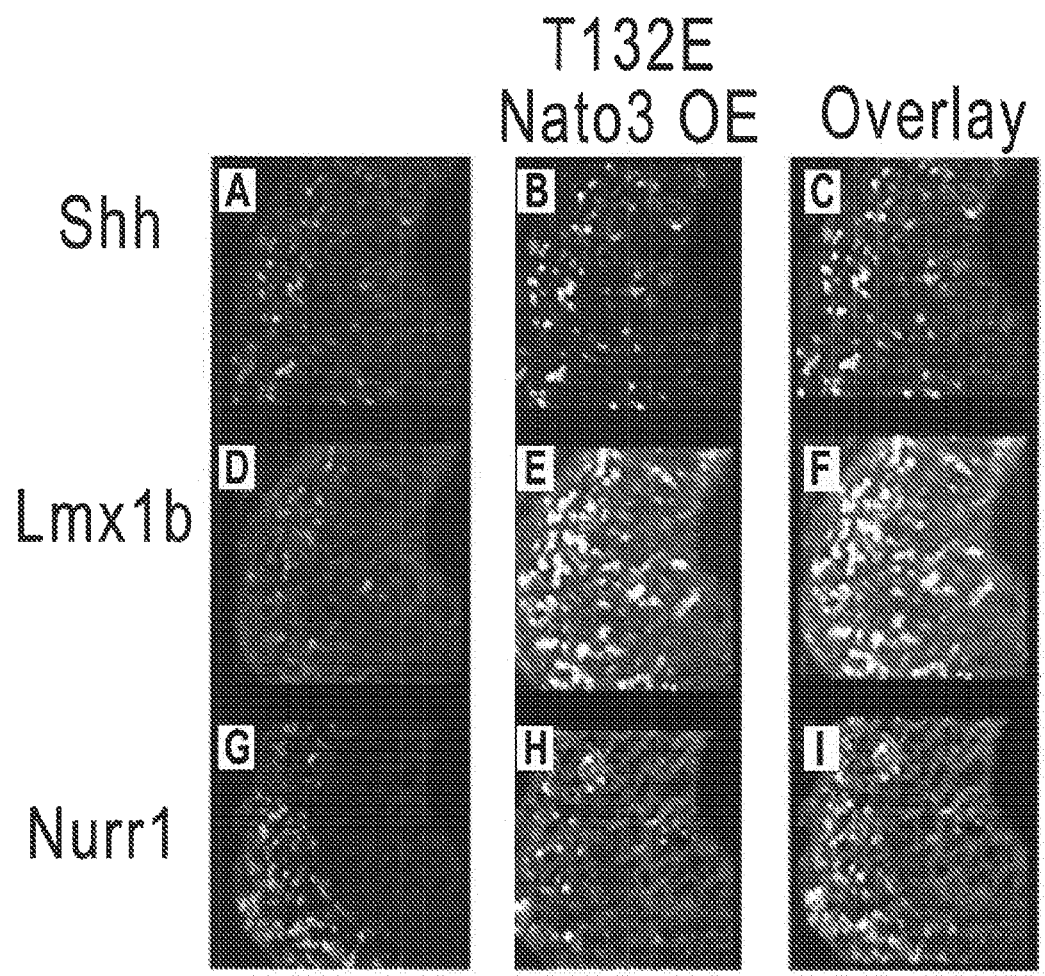
FIG. 4 depicts photomicrographs of chicken embryonic spinal cord tissue sections stained with antibodies to progenitor marker expression such as Shh, Lmx1b, and Nurr1 after the addition of T101E/T132E (double mutant) Nato3 mutant polypeptide stained in panels B, E and H. Expression of floor plate markers Shh, Lmx1b and Nurr1 were stained with specific fluorescence antibodies shown in panels A, D, and G, and the presence of the Nato3 mutant polypeptide shown in panels B, E, and H are overlayed in panels C, F, and I.

Example 4—T101E/T132E (Double Mutant) May Induce Floor Plate Markers in the Spinal Cord where the Wild-Type Nato3 Cannot In the spinal cord, we inspected the ability of T101E/T132E (double mutant) to induce ectopic expression of Foxa2, a floor plate cell marker, in cells that were overexpressing T101E/T132E (double mutant). FIG. 4 demonstrates that overexpression of wild-type Nato3 does not induce expression of Foxa2 in the spinal cord. In the case of the mutant T101E/T132E (double mutant), there is a significant induction of Foxa2 expression in the T101E/T132E (double mutant) overexpressing side of the spinal cord, extending to the dorsal region of the spinal cord. A higher magnification image is shown in FIG. 4, of the effect of T101E/T132E (double mutant) seen in FIG. 3. Strong colocalization is seen between the T101E/T132E (double mutant) overexpression and the markers Shh (See FIG. 4, Panel C) and Lmx1b (Panel F; ~99% for both markers; n=3). Nurr1 induction was not detectable by T101E/T132E (See FIG. 4, Panels G, H, I). It may be that T101E/T132E (double mutant) Nato3 may drive cells to become dopamine neuron progenitors, but either not permit maturation, or prevent them from maturing. Additionally, GFP+/Foxa2+ double positive cells may also be seen in the dorsal root ganglion, well outside of the area of the spinal cord is transfected by the electroporation technique.

Figure 5:
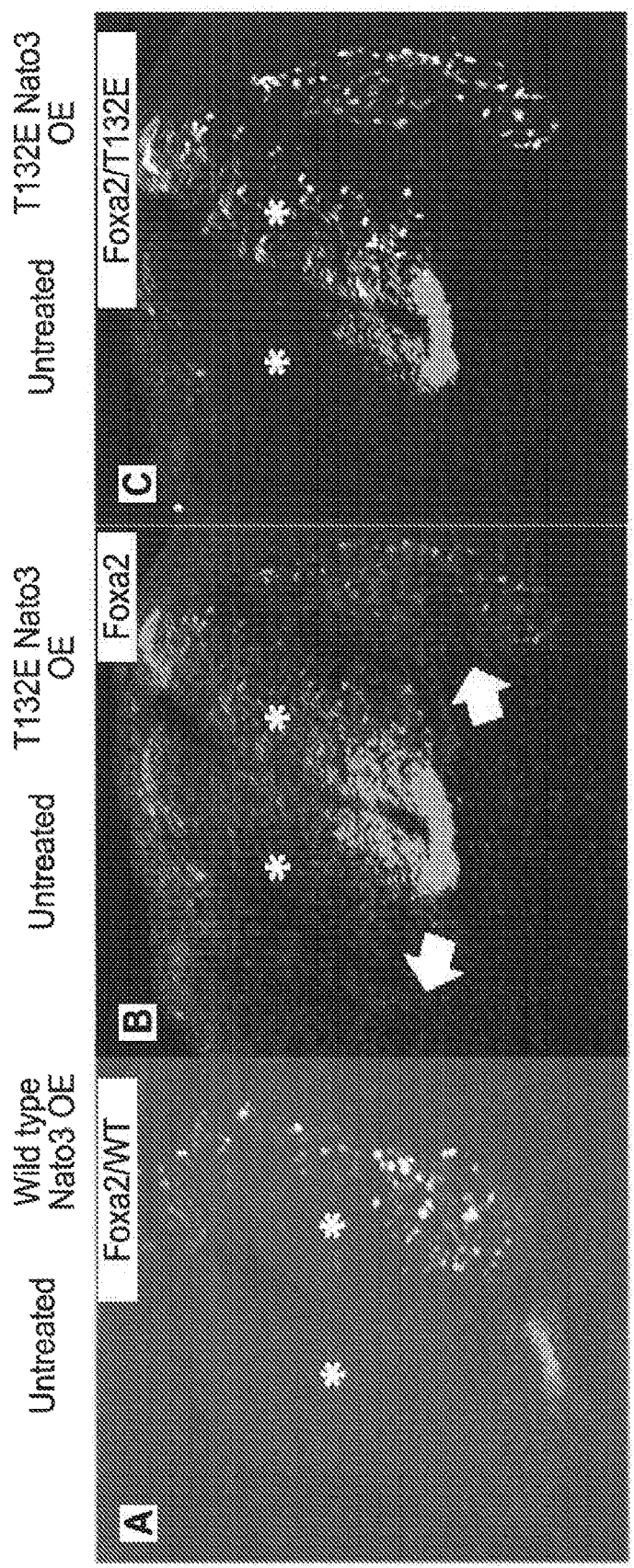
FIG. 5 depicts photomicrographs of chicken embryonic spinal cord tissue sections stained with antibodies to Foxa2 in posterior neural tube tissue sections containing wild-type Nato3 over-expression compared to T101E/T132E (double mutant) Nato3 mutant polypeptide expression in the same posterior neural tube sections.

As shown in FIG. 5, T101E/T132E (double mutant) Nato3 overexpression may induce floor plate and DA neuron progenitor markers in the spinal cord. The posterior neural tube (embryonic spinal cord) treated with wild-type Nato3 overexpression represented in panel A of FIG. 5 with regions of symmetry between the treated and untreated sides indicated with asterisks. There was no induction of Foxa2 by WT Nato3 overexpression. Panel B of FIG. 5, depicts mutant Nato3 overexpression showing ectopic expression of Foxa2 (expression appears as punctate expression), a marker for floor plate cells and DA neuron progenitors. Overlay of treated cells with Foxa2 expression appears as yellow as shown in panel C. This is particularly noticeable in the dorsal neural tube, where Foxa2 is not typically expressed (see asterisks in panel B), and the sensory ganglia of the peripheral nervous system. The left bracket indicates position of treated sensory ganglia (compare arrowheads in panel B. Similar results are obtained with Shh, which marks floor plate cells, and Lmx1b, which marks midbrain floor plate cells that are DA neuron progenitors as well as DA neurons. This action on these three markers occurs in all regions of the neural tube that were tested (spinal cord, hindbrain, midbrain, telencephalon), indicating that the effect of Nato3 mutant polypeptide expression is highly potent in a broad array of neural progenitors.

This indicates that T101E/T132E (double mutant) Nato3 overexpressing cells have migrated from the neural tube towards the peripheral nervous system, similar to the type of migration seen by neural crest stem cells as they delaminate from the dorsal neural tube and populate the peripheral nervous system. Similar expression patterns of induction of ectopic expression by T101E/T132E (double mutant) Nato3 was seen with Lmx1b, but there was no induction of Nurr1 expression in the spinal cord, similar to results seen in the midbrain (data not shown).

Figure 6:
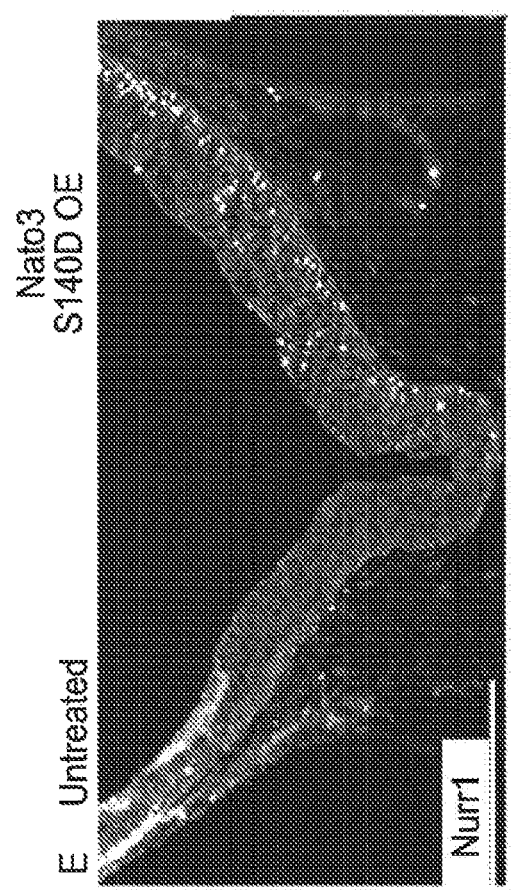
FIG. 6 depicts photomicrographs of chicken embryonic midbrain and forebrain tissue sections stained with antibodies to Nurr1 in embryonic midbrain tissue sections containing untreated compared to T101E/S140D (double mutant) Nato3 mutant polypeptide over expression. Panel A depicts immunofluorescence staining Nurr1 expression in the untreated (left) and treated (right) regions of the anterior portion of the midbrain of embryonic brain tissue sections. The bright dots seen in panel A indicate the expression of Nurr1+, a dopamine neuron marker, by neural progenitors in that region of tissue. These dots are not seen on the untreated side, indicating that S140D Nato3 may induce Nurr1 expression from neural progenitors that normally would not differentiate into DA neurons. Panel B depicts Nato3 T101E/S140D (double mutant) expression (in panel "B") staining which overlaps with Nurr1 (in panel "B") staining at 98+2% frequency in this region of the midbrain. Similar results are seen in forebrain tissue sections.
Figure 6:
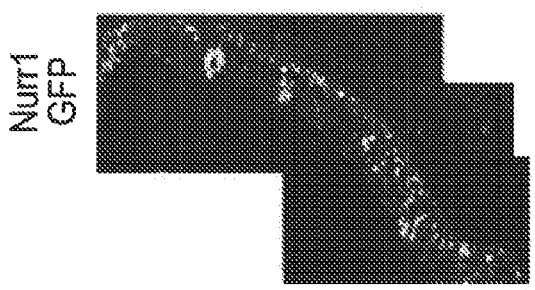
Figure 7:
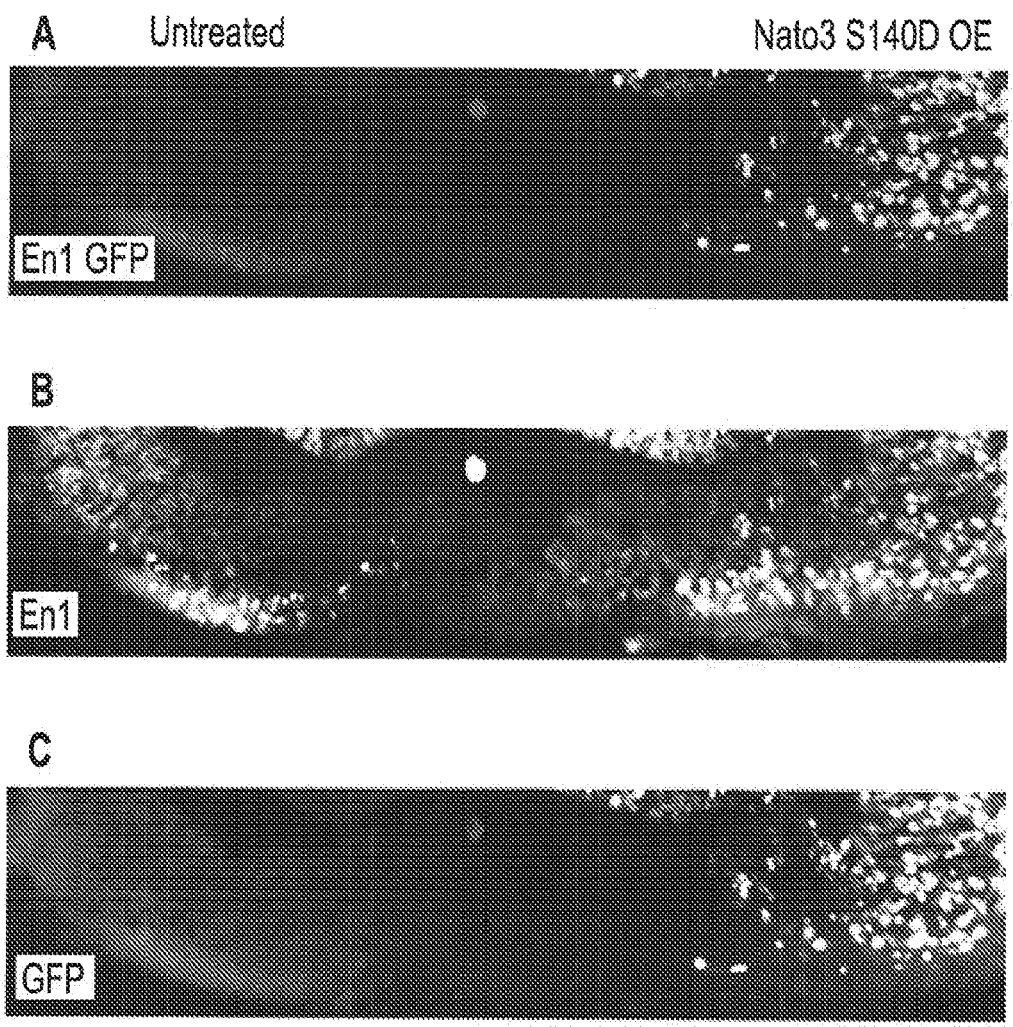
FIG. 7 depicts photomicrographs of chicken embryonic neural tube sections stained with antibodies to progenitor marker expression such as En1 after the untreated and Nato3S140D over expression (OE) tissue sections. In En1 expression (in panels A, and B) is induced in the Nato3 T101E/S140D (double mutant) transfected region ("Nato3 T101E/S140D (double mutant) OE", overlay indicated as well) of the posterior midbrain relative to the internal negative control ("Untreated"). Ectopic expression of En1 (panels A and B) where Nato3 T101E/S140D (double mutant) expression (panel A; and panel C) is present, adding to the number of En1 positive cells typically see in in the posterior midbrain (Panel A shows induced ectopic expression of En1 (panel A; and panel B).

Example 5—T101E/S140D (Double Mutant) Nato3 Induces Expression of Nurr1 Throughout the Rostral Nervous System To test the effect of a mutation at a second putative phosphorylation site, we modified the serine at position 140 (S140) to a negatively charged amino acid (aspartate, D) and modified the threonine at position 101 and mutated that amino acid to glutamic acid (E) creating the T101E/S140D (double mutant) Nato3. Overexpression of T101E/S140D (double mutant) Nato3 demonstrated tremendous induction of immature DA neuron marker Nurr1 in the posterior and anterior midbrain (FIG. 6). This effect differs from that seen with the T101E/T132E (double mutant) Nato3 overexpression (see FIGS. 3C & 4G-I) with little to no effect on Nurr1 expression, or the anatomically restricted induction of Nurr1 expression seen with the wild-type Nato3 in the posterior midbrain. For T101E/S140D (double mutant) Nato3 is able to induce Nurr1 expression in the anterior ventral midbrain and even telencephalon (data not shown) as well as the posterior ventral midbrain. As shown in FIG. 6, the percent co-localization of Nurr1+/GFP+cells is 98+2% in the anterior region of the midbrain and 99% colocalization in the posterior midbrain (n=3). To aid comparison, brackets in panel (A) indicate region of symmetry between untreated (on the left) and treated (on the right) side of the embryo. The bright dots seen in panel A indicate the expression of Nurr1+a dopamine neuron marker, by neural progenitors in that region of tissue. These dots are not seen on the untreated side, indicating that T101E/S140D (double mutant) Nato3 may induce Nurr1 expression from neural progenitors that normally would not differentiate into DA neurons. Nato3 T101E/S140D (double mutant) expression (in panel "B") overlaps with Nurr1 (in panel "B") at 98+2% frequency in this region of the midbrain.

Example 6—Conclusion/Discussion

The above data show that specific mutants of the protein Nato3 may induce floor plate, DA neuron progenitor and DA neuron markers broadly in the nervous system. These data suggest that physiological phosphorylation of Nato3 may be responsible for inducing DA neuron generation in the developing nervous system and offer some promise for therapeutic strategies to generate new DA neurons from embryonic stem cells (ESCs) or induced pluripotent stem cells (iPSCs) in cell replacement therapies. Mutation of the threonine at position 101 and 132 to the negatively charged amino acid glutamate (T101E/T132E) imparted the ability of Nato3 to induce floor plate and DA progenitor markers Shh and Lmx1b in the midbrain, but had little to no effect on Nurr1 expression. Mutation of the threonine at position 101 and serine at position 140 to a negatively charged amino acid (T101E and aspartate S140D) imparted the ability of Nato3 to induce the immature DA neuron marker Nurr1 broadly in the midbrain and forebrain. The effects of these mutations differ from that seen with the wild type Nato3. Wild-type Nato3 could induce some modest floor plate cell markers (Shh and Foxa2) only in the posterior ventral midbrain, near the midbrain hindbrain boundary and with very low frequency. This is attributed to local factors within that domain that regulate the activity of Nato3. Because phosphorylation may induce transient changes in response to local factors, it may be that in the physiological context, phosphorylation of wild-type Nato3 at the amino acid T101 and T132 could induce the generation of floor plate cell lineage, and phosphorylation at T101 and amino acid S140 could promote the induction of DA neuron progenitor and DA neuron differentiation.

Promotion of dopamine neuron linage markers is also seen in the human species form of the Nato3 gene, in the mutation of the serine 138 to aspartate (S138D) compared to the action of the wild type form of the human Nato3 gene.

Creating mutations at specific serine, threonine and tyrosine residues may be useful to characterize the effects of phosphorylation at putative phosphoacceptor sites (McKay and Morrison, 2007). However, in vivo characterization is particularly important because many mutations do not adequately mimic the phosphorylation state of the protein, in part because the negative charge with an amino acid may not be present at physiological pH, and the size of the phosphate group is different than negatively charged sidechain of an amino acid like aspartate or glutamate (Dephoure et al., 2013).

Examination of other bHLH proteins suggest that phosphorylation at the mouse S140 or human S138 could affect the stability of the E47-Nato3 dimer, as is the case when the serine homologous to S140 is mutated in Ascl1. Further, the selection of dimerization partners of either homodimerization or dimerization with E47 is affected by phosphorylation at a serine homologous to S140 in the Olig2 bHLH protein.

The differences between the Nato3 mutants T101E/T132E and T101E/S140D described herein may be due to subtle differences in the position of the residues on the protein. When the Nato3 amino acid sequence is aligned with the NeuroD crystal structure of the basic helix loop helix, T132 is in the loop region whereas S140 is in the amino termini of helix 2. S140 is closer to the phosphate backbone of DNA binding site, which might exert repulsion and disrupt DNA binding. This kind of disruption could exert a dominant negative effect on the protein function.

Example 7. Effect of Human Nato3 Mutants on Driving Dopaminergic Neuron Lineage Marker Expression To determine if phosphomimetic mutations of human Nato3 gene shows the same potential to drive DA neuron lineage marker expression as the mouse Nato3 gene, we tested genes that encoded for the human wild type Nato3 and human S138D Nato3 gene by overexpression in the developing chick embryo as described in Example 1. S138 is homologous to the S140 position in the mouse Nato3 protein. Compared to the human wild type S138, the S138D mutant shows induction of dopamine neuron progenitor markers such as Shh. This illustrates the potential of phosphomimetic mutations in human Nato3 to drive DA neuron progenitor lineage.

Figure 8A:
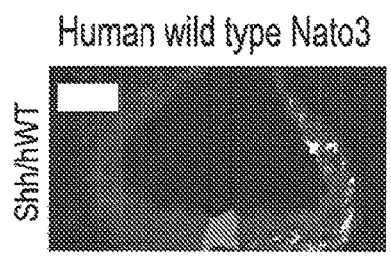
FIGS. 8A-8L show immunofluorescence photomicrographs of chicken embryonic neural tube sections stained with antibodies to progenitor marker expression such as Shh and Nurr1 after the untreated and human Nato3 S138D over expression (OE) tissue sections. Overexpression of the human wild type Nato3 gene did not induce Shh strongly (compare "Shh" between FIGS. 8A, 8D, and 8E compared to FIGS. 8B, 8E and 8H). Overlay is shown in the top row between the transfected cells and the lineage marker; Shh in FIGS. 8A and 8B and Nurr1 in FIGS. 8C and 8J). The induction of expression of dopamine neuron lineage marker expression is in the middle row ("Shh" in FIGS. 8D & 8E; and expression of "Nurr1" in FIGS. 8F and 8K). The transfection of the gene of interest is indicated in the bottom row shown in FIGS. 8G, 8H, 8I, and 8L.
Figure 8B:
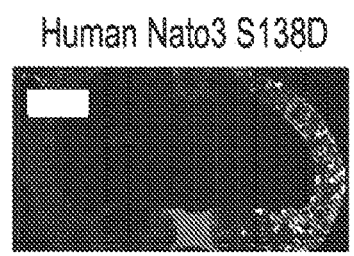
Figure 8D:
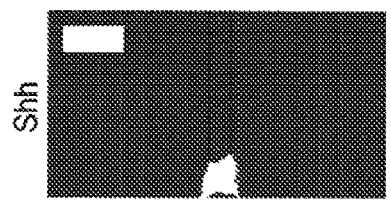
Figure 8E:
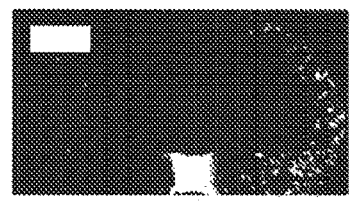
Figure 8G:
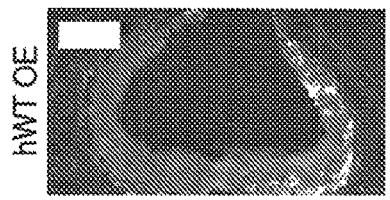
Figure 8H:
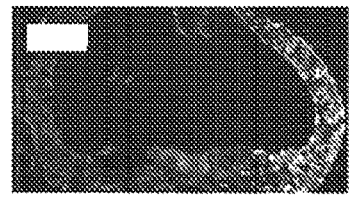
Figure 8C:
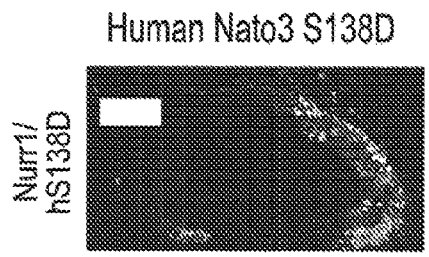
Figure 8J:
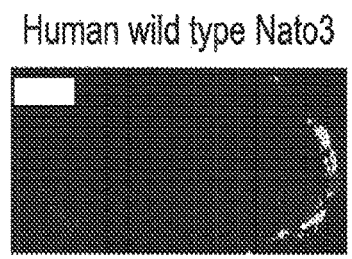
Figure 8F:
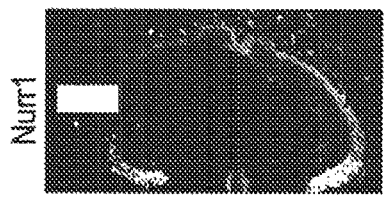
Figure 8K:
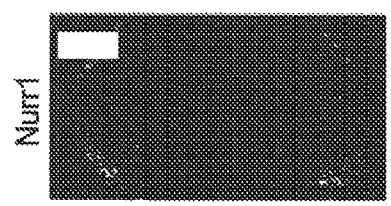
Figure 8I:
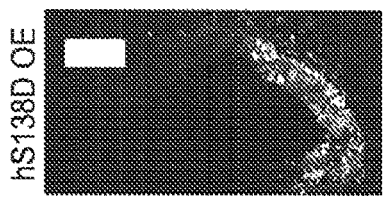
Figure 8L:
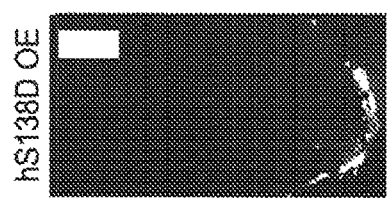

FIGS. 8A-8I show the expression of the marker Shh. Like the mouse wild type Nato3 gene, overexpression of the human wild type Nato3 gene did not induce Shh strongly (compare "Shh" between FIGS. 8A, 8D, and 8E compared to FIGS. 8B, 8E and 8H). Overlay is shown in the top row between the transfected cells and the lineage marker; Shh in FIGS. 8A and 8B; and the marker Nurr1 in FIGS. 8C and 8J). The induction of expression of dopamine neuron lineage marker expression is in the middle row ("Shh" in FIGS. 8D & 8E; and expression of "Nurr1" in FIGS. 8F and 8K). The transfection of the gene of interest is indicated in the bottom row shown in FIGS. 8G, 8H, 8I and 8L.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the claims.

1. Embodiment 1, an isolated mutant Nato3 polypeptide, the polypeptide comprising at least one mutation in any one or more of serine, threonine or tyrosine amino acid residues in the HLH domain defined by amino acids 99 to 158 of SEQ ID NOs: 1-5, or any variant, derivative, or ortholog thereof, with the proviso that the mutant Nato3 polypeptide with only one mutation is not a mutation of S140D in SEQ ID NO: 2.

2. Embodiment 2, the isolated mutant Nato3 polypeptide according to embodiment 1, wherein the at least one mutation occurs in SEQ ID NO: 1-2.

3. Embodiment 3, the isolated mutant Nato3 polypeptide according to any one of embodiments 1 or 2, wherein the mutation occurs at a serine, threonine or both.

4. Embodiment 4, the isolated mutant Nato3 polypeptide according to any one of embodiments 1 or 2, wherein the mutation occurs at position 99, 130, or 138, or combinations thereof of SEQ ID NO: 1.

5. Embodiment 5, the isolated mutant Nato3 polypeptide according to embodiment 4, wherein the mutation occurs at position 99.

6. Embodiment 6, the isolated mutant Nato3 polypeptide according to embodiment 5, wherein threonine at position 99 is substituted with glutamic acid, or aspartic acid.

7. Embodiment 7, the isolated mutant Nato3 polypeptide according to embodiment 6, wherein threonine at position 99 is substituted with glutamic acid.

8. Embodiment 8, the isolated mutant Nato3 polypeptide according to embodiment 6, wherein threonine at position 99 is substituted with aspartic acid.

9. Embodiment 9, the isolated mutant Nato3 polypeptide according to embodiment 4, wherein the mutation occurs at position 130.

10. Embodiment 10, the isolated mutant Nato3 polypeptide according to embodiment 9, wherein threonine at position 130 is substituted with glutamic acid, or aspartic acid.

11. Embodiment 11, the isolated mutant Nato3 polypeptide according to embodiment 10, wherein threonine at position 130 is substituted with glutamic acid.

12. Embodiment 12, the isolated mutant Nato3 polypeptide according to embodiment 10, wherein threonine at position 130 is substituted with aspartic acid.

13. Embodiment 13, the isolated mutant Nato3 polypeptide according to embodiment 4, wherein the mutation occurs at position 138.

14. Embodiment 14, the isolated mutant Nato3 polypeptide according to embodiment 13, wherein serine at position 138 is substituted with glutamic acid, or aspartic acid.

15. Embodiment 15, the isolated mutant Nato3 polypeptide according to embodiment 14, wherein serine at position 138 is substituted with glutamic acid.

16. Embodiment 16, the isolated mutant Nato3 polypeptide according to embodiment 14, wherein threonine at position 138 is substituted with aspartic acid.

17. Embodiment 17, the isolated mutant Nato3 polypeptide according to any one of embodiments 1 or 2, wherein the mutation occurs at position 101, 132 or 140, or combinations thereof of SEQ ID NO: 2.

18. Embodiment 18, the isolated mutant Nato3 polypeptide according to embodiment 17, wherein the mutation occurs at position 101.

19. Embodiment 19, the isolated mutant Nato3 polypeptide according to embodiment 18, wherein threonine at position 101 is substituted with glutamic acid, or aspartic acid.

20. Embodiment 20, the isolated mutant Nato3 polypeptide according to embodiment 19, wherein threonine at position 101 is substituted with glutamic acid.

21. Embodiment 21, the isolated mutant Nato3 polypeptide according to embodiment 19, wherein threonine at position 101 is substituted with aspartic acid.

22. Embodiment 22, the isolated mutant Nato3 polypeptide according to embodiment 17, wherein the mutation occurs at position 132.

23. Embodiment 23, the isolated mutant Nato3 polypeptide according to embodiment 22, wherein threonine at position 132 is substituted with glutamic acid, or aspartic acid.

24. Embodiment 24, the isolated mutant Nato3 polypeptide according to embodiment 23, wherein threonine at position 132 is substituted with glutamic acid.

25. Embodiment 25, the isolated mutant Nato3 polypeptide according to embodiment 23, wherein threonine at position 132 is substituted with aspartic acid.

26. Embodiment 26, the isolated mutant Nato3 polypeptide according to embodiment 17, wherein the mutation occurs at position 140.

27. Embodiment 27, the isolated mutant Nato3 polypeptide according to embodiment 13, wherein serine at position 140 is substituted with glutamic acid.

28. Embodiment 28, an isolated mutant Nato3 polypeptide, the polypeptide comprising two mutations in two of serine, threonine or tyrosine amino acid residues in the HLH domain defined by amino acid sequences 99 to 158 of SEQ ID NOs: 1-5, or any variant, derivative, or ortholog thereof.

29. Embodiment 29, the isolated mutant Nato3 polypeptide according to embodiment 28, wherein the mutations occur in two amino acids selected from T101, T132 and S140 of SEQ ID NO:2.

30. Embodiment 30, the isolated mutant Nato3 polypeptide according to embodiment 28, wherein the mutations occur in two amino acids selected from T99, T130 and S138 of SEQ ID NO:1.

31. Embodiment 31, the isolated mutant Nato3 polypeptide according to any one of embodiments 28-30, wherein the mutations comprises substituting the wild-type amino acids serine, threonine or tyrosine within the HLH domain defined by amino acid sequences 99 to 158 of SEQ ID NOs: 1-5, with amino acids glutamic acid or aspartic acid.

32. Embodiment 32. A method of stimulating a population of brain cells to differentiate into dopaminergic progenitor neuronal cells or dopaminergic neuronal cells, the method comprising increasing phosphorylation of Nato3 in the brain cells and culturing the brain cells until a progenitor dopaminergic neuronal cell marker or a dopaminergic neuronal cell marker is expressed in the cultured brain cells.

33. Embodiment 33, the method according to embodiment 32, wherein increasing phosphorylation of Nato3 in the brain cells comprises expressing a Nato3 mutant polypeptide of embodiments 1-32, or a Nato3 mutant polynucleotide which encodes a Nato3 mutant polypeptide of embodiments 1-32 in the brain cells.

34. Embodiment 34, the method according to any one of embodiments 32-33, wherein brain cells are stem cells.

35. Embodiment 35, the method according to any one of embodiments 32-34, wherein brain cells are isolated from the brain floor plate.

36. Embodiment 36, the method according to any one of embodiments 32-35, wherein expressing a Nato3 mutant polypeptide or Nato3 mutant polynucleotide in the brain cells comprises introducing into the brain cells at least one polynucleotide operable to encode a mutant Nato3 polypeptide of embodiments 1-32.

37. Embodiment 37, the method of embodiment 36, wherein expressing a Nato3 mutant polypeptide or Nato3 mutant polynucleotide in the brain cells is made by transfecting or transforming the brain cells with an expression vector which comprises a polynucleotide sequence which encodes a mutant Nato3 polypeptide of embodiments 1-32.

38. Embodiment 38, the method of any one of embodiments 32-37, wherein expression of a progenitor dopaminergic neuronal cell marker in the brain cells comprises an expression of at least one marker selected from the group consisting of Shh, Lmx1b, and Foxa2.

39. Embodiment 39, the method of any one of embodiments 32-38, wherein the dopaminergic progenitor neuronal cells are determined to be differentiated when at least 50% of the population of brain cells express at least one marker selected from the group consisting of Shh, Lmx1b, and Foxa2.

40. Embodiment 40, the method of any one of embodiments 32-39, wherein the dopaminergic neuronal cells are determined to be differentiated when at least 50% of the population of brain cells express Nurr1.

41. Embodiment 41, the method of any one of embodiments 32-40, wherein increasing phosphorylation of Nato3 in the brain cells comprises increasing the expression or activity of a protein kinase for phosphorylating Nato3 in the brain cells.

42. Embodiment 42, the method of embodiment 40, wherein increasing phosphorylation of Nato3 in the brain cells comprises expressing an endogenous or heterologous protein kinase operable to increase phosphorylation of Nato3.

43. Embodiment 43, a genetically modified isolated population of dopaminergic neuron progenitors and/or dopaminergic neurons, the isolated population comprising a mutant Nato3 polypeptide, as set forth in embodiments 1-32, and wherein the population of dopaminergic neuron progenitors and/or dopaminergic neurons express at least one marker selected from Shh, Lmx1b, and Foxa2 in at least 50% of the population.

44. Embodiment 44, a method for treating or preventing Parkinson's disease (PD) in a subject in need thereof, comprising administering to the subject, a therapeutically effective amount of a composition comprising a mutant Nato3 polypeptide as set forth in embodiments 1-32, or a polynucleotide construct encoding the mutant Nato3 polypeptide as set forth in embodiments 1-32.

What is claimed is:

1. An isolated mutant Nato3 polypeptide, the polypeptide comprising at least one mutation in any one or more serine or threonine amino acid residues in the HLH domain defined by amino acids 99 to 158 of SEQ ID NO: 1, wherein the at least one mutation comprises a substitution of serine or threonine with either aspartic acid or glutamic acid.

2. The isolated mutant Nato3 polypeptide according to claim 1, wherein the at least one mutation occurs at position 99, 130, or 138, or combinations thereof of SEQ ID NO: 1.

3. The isolated mutant Nato3 polypeptide according to claim 2, wherein the at least one mutation occurs at position 99.

4. The isolated mutant Nato3 polypeptide according to claim 2, wherein the at least one mutation occurs at position 130.

5. The isolated mutant Nato3 polypeptide according to claim 2, wherein the at least one mutation occurs at position 138.

6. An isolated mutant Nato3 polypeptide, the polypeptide comprising at least one mutation in any one or more serine or threonine amino acid residues in the HLH domain defined by amino acids 99 to 158 of SEQ ID NO: 2, wherein the at least one mutation comprises a substitution of serine or threonine with either aspartic acid or glutamic acid.

7. The isolated mutant Nato3 polypeptide according to claim 6, wherein the at least one mutation occurs at position 101, 132, or 140, or combinations thereof of SEQ ID NO: 2.

8. The isolated mutant Nato3 polypeptide according to claim 7, wherein the at least one mutation occurs at position 101.

9. The isolated mutant Nato3 polypeptide according to claim 7, wherein the at least one mutation occurs at position 132.

10. The isolated mutant Nato3 polypeptide according to claim 7, wherein the at least one mutation occurs at position 140.

11. A method of stimulating a population of brain cells to differentiate into dopaminergic progenitor neuronal cells or dopaminergic neuronal cells, the method comprising expressing a Nato3 mutant polypeptide according to claim 1 or 6 in the brain cells and culturing the brain cells until a progenitor dopaminergic neuronal cell marker or a dopaminergic neuronal cell marker is expressed in the cultured brain cells.

12. The method according to claim 11, wherein brain cells are stem cells.

13. The method according to claim 11, wherein brain cells are isolated from the brain floor plate.

14. The method according to claim 11, wherein expressing the Nato3 mutant polypeptide in the brain cells comprises introducing into the brain cells at least one polynucleotide which encodes a mutant Nato3 polypeptide according to claim 1 or 6.

15. The method according to claim 14, wherein expressing the Nato3 mutant polypeptide in the brain cells comprises transfecting or transforming the brain cells with an expression vector which comprises a polynucleotide sequence which encodes a mutant Nato3 polypeptide according to claim 1 or 6.

16. The method according to claim 11, wherein expression of a progenitor dopaminergic neuronal cell marker in the brain cells comprises an expression of at least one marker selected from the group consisting of Shh, Lmx1b, and Foxa2.

17. The method according to claim 11, wherein the dopaminergic progenitor neuronal cells are determined to be differentiated when at least 50% of the population of brain cells express at least one marker selected from the group consisting of Shh, Lmx1b, and Foxa2.

18. The method according to claim 11, wherein the dopaminergic neuronal cells are determined to be differentiated when at least 50% of the population of brain cells express Nurr1.

19. A genetically modified isolated population of dopaminergic progenitor neurons, the isolated population comprising the mutant Nato3 polypeptide according to claim 1 or 6.

20. A method for treating Parkinson's disease (PD) in a subject in need thereof, comprising administering to the subject a therapeutically effective amount of a composition comprising the mutant Nato3 polypeptide of claim 1 or 6.

* * * * *

```
                          SEQUENCE LISTING

<160> NUMBER OF SEQ ID NOS: 27

<210> SEQ ID NO 1
<211> LENGTH: 166
<212> TYPE: PRT
<213> ORGANISM: Homo sapiens
<220> FEATURE:
<221> NAME/KEY: MISC_FEATURE
<222> LOCATION: (1)..(166)
<223> OTHER INFORMATION: NCBI Accession No. NP_690862

<400> SEQUENCE: 1

Met Ala Ala Tyr Pro Glu Ser Cys Val Asp Thr Thr Val Leu Asp Phe
1               5                   10                  15

Val Ala Asp Leu Ser Leu Ala Ser Pro Arg Pro Leu Leu Cys Asp
            20                  25                  30

Phe Ala Pro Gly Val Ser Leu Gly Asp Pro Ala Leu Ala Leu Arg Glu
        35                  40                  45

Gly Arg Pro Arg Met Ala Arg Phe Glu Glu Gly Asp Pro Glu Glu
    50                  55                  60

Glu Glu Cys Glu Val Asp Gln Gly Asp Gly Glu Glu Glu Glu Glu
65                  70                  75                  80

Glu Arg Gly Arg Gly Val Ser Leu Leu Gly Arg Pro Lys Arg Lys Arg
                85                  90                  95

Val Ile Thr Tyr Ala Gln Arg Gln Ala Ala Asn Ile Arg Glu Arg Lys
            100                 105                 110

Arg Met Phe Asn Leu Asn Glu Ala Phe Asp Gln Leu Arg Arg Lys Val
        115                 120                 125

Pro Thr Phe Ala Tyr Glu Lys Arg Leu Ser Arg Ile Glu Thr Leu Arg
    130                 135                 140

Leu Ala Ile Val Tyr Ile Ser Phe Met Thr Glu Leu Leu Glu Ser Cys
145                 150                 155                 160

Glu Lys Lys Glu Ser Gly
                165

<210> SEQ ID NO 2
<211> LENGTH: 168
<212> TYPE: PRT
<213> ORGANISM: Mus musculus

<400> SEQUENCE: 2

Met Ala Ala Tyr Pro Glu Ser Cys Leu Asp Ala Thr Val Leu Asn Phe
1               5                   10                  15

Val Ala Asp Leu Ser Leu Ala Ser Pro Arg His Pro Leu Leu Cys Glu
            20                  25                  30

Phe Pro Pro Gly Val Pro Phe Gly Asp Arg Thr Leu Gly Tyr Arg Glu
        35                  40                  45

Gly Arg Pro Gly Arg Leu Ser Gln Phe Asp Glu Arg Tyr Gln Glu Val
    50                  55                  60

Glu Gly Asp Glu Val Glu Tyr Glu Asp Pro Glu Glu Glu Glu Glu
65                  70                  75                  80

Gly Glu Gly Arg Gly Arg Val Ala Ser Leu Leu Gly Arg Pro Lys Arg
                85                  90                  95
```

```
Lys Arg Val Ile Thr Tyr Ala Gln Arg Gln Ala Ala Asn Ile Arg Glu
            100                 105                 110

Arg Lys Arg Met Phe Asn Leu Asn Glu Ala Phe Asp Gln Leu Arg Arg
        115                 120                 125

Lys Val Pro Thr Phe Ala Tyr Glu Lys Arg Leu Ser Arg Ile Glu Thr
    130                 135                 140

Leu Arg Leu Ala Ile Val Tyr Ile Ser Phe Met Thr Glu Leu Leu Gln
145                 150                 155                 160

Ser Lys Glu Glu Lys Glu Ala Ser
                165

<210> SEQ ID NO 3
<211> LENGTH: 166
<212> TYPE: PRT
<213> ORGANISM: Rattus norvegicus

<400> SEQUENCE: 3

Met Ala Ala Tyr Pro Glu Ser Cys Leu Asp Ala Asn Val Leu Asn Phe
1               5                   10                  15

Val Ala Asp Leu Ser Leu Ala Ser Pro Arg His Pro Phe Leu Cys Glu
            20                  25                  30

Phe Pro Pro Gly Val Pro Phe Glu Asp Gln Thr Leu Gly Phe Arg Glu
        35                  40                  45

Gly Arg Gly Leu Leu Gln Phe Glu Gly Arg Tyr Gln Glu Val Glu Gly
    50                  55                  60

Gly Glu Val Asp Tyr Glu Asp Pro Glu Glu Glu Glu Glu Glu Gly Glu
65                  70                  75                  80

Gly Arg Gly Arg Val Ala Ser Leu Leu Gly Arg Pro Lys Arg Lys Arg
                85                  90                  95

Val Ile Thr Tyr Ala Gln Arg Gln Ala Ala Asn Ile Arg Glu Arg Lys
            100                 105                 110

Arg Met Phe Asn Leu Asn Glu Ala Phe Asp Gln Leu Arg Arg Lys Val
        115                 120                 125

Pro Thr Phe Ala Tyr Glu Lys Arg Leu Ser Arg Ile Glu Thr Leu Arg
    130                 135                 140

Leu Ala Ile Val Tyr Ile Ser Phe Met Thr Glu Leu Leu Gln Ser Lys
145                 150                 155                 160

Glu Glu Lys Glu Ala Ser
                165

<210> SEQ ID NO 4
<211> LENGTH: 183
<212> TYPE: PRT
<213> ORGANISM: Gallus gallus

<400> SEQUENCE: 4

Met Ser Ala Gly Leu Phe Pro Ala His Arg Pro Glu Leu Leu Arg
1               5                   10                  15

Gly Thr Ala Pro Pro Leu Pro Cys Pro Glu Arg Leu Leu Gly Ala Ser
            20                  25                  30

Val Leu Gly Phe Val Ala Asp Ile Ser Leu Gly Ala Pro Gln Ser Ser
        35                  40                  45

Ser Arg Ala Gly Pro Ser Leu Gly Leu Thr Ser Glu Pro Pro Phe Gly
    50                  55                  60

Asp Arg Thr Leu Ser Leu Arg Glu Gly Met Ala Arg Gly Leu Pro Leu
65                  70                  75                  80
```

Ala Ala Phe Gly Asp Gly Asp Leu Glu Asp Glu Glu Glu Glu
                85                  90                  95

Glu Glu Arg Met Arg Ser Ala Ser Leu Leu Asp Arg Pro Arg Arg Lys
            100                 105                 110

Arg Val Ile Thr Tyr Ala Gln Arg Gln Ala Ala Asn Ile Arg Glu Arg
            115                 120                 125

Lys Arg Met Phe Asn Leu Asn Glu Ala Phe Asp Gln Leu Arg Lys Lys
130                 135                 140

Val Pro Thr Phe Ala Tyr Glu Lys Arg Leu Ser Arg Ile Glu Thr Leu
145                 150                 155                 160

Arg Leu Ala Ile Val Tyr Ile Ser Phe Met Thr Glu Leu Leu Asn Gly
                165                 170                 175

Cys Ser Arg Gln Glu Ala Ser
            180

<210> SEQ ID NO 5
<211> LENGTH: 195
<212> TYPE: PRT
<213> ORGANISM: Drosophila melanogaster

<400> SEQUENCE: 5

Met Gln His Pro His Pro Ile Asp Gln Pro Thr Tyr Met Pro Asp Val
1               5                   10                  15

Pro Phe Gln Pro Leu Trp Gly Gln Glu Ala Pro Pro Pro Ile Val
            20                  25                  30

Pro Tyr Gln Glu Leu Ile Ala Gly Phe Pro Cys Thr Asp Leu Ser Leu
            35                  40                  45

Trp Gln Arg Ser Gln Val Thr Pro Leu Val Pro Gln Arg Pro Ser Thr
50                  55                  60

Asn Gly Arg Ala Asn Gly Ser Ser Ser Ser Lys Lys Thr Arg Arg
65                  70                  75                  80

Arg Val Ala Ser Met Ala Gln Arg Ala Ala Asn Ile Arg Glu Arg
                85                  90                  95

Arg Arg Met Phe Asn Leu Asn Glu Ala Phe Asp Lys Leu Arg Arg Lys
            100                 105                 110

Val Pro Thr Phe Ala Tyr Glu Lys Arg Leu Ser Arg Ile Glu Thr Leu
            115                 120                 125

Arg Leu Ala Ile Thr Tyr Ile Gly Phe Met Ala Glu Leu Leu Ser Gly
            130                 135                 140

Thr Pro Ser Asn Ser His Lys Ser Arg Ser Asp Val Tyr Gly Ser Met
145                 150                 155                 160

Asn Gly His His Gln Ala Pro Pro Ala Ile His Pro His Leu
                165                 170                 175

His Pro Ala Ala Ala Tyr Gln Arg Asp Phe Ala Ser Pro Tyr Asn His
            180                 185                 190

Ser Leu Ser
        195

<210> SEQ ID NO 6
<211> LENGTH: 507
<212> TYPE: DNA
<213> ORGANISM: Artificial Sequence
<220> FEATURE:
<223> OTHER INFORMATION: T101E mutant mouse Nato3 polynucleotide

<400> SEQUENCE: 6

```
atggccgcct atccagagag ctgcttggat gctaccgtgc tgaacttcgt agcagatctc    60
tctctggcct ctcccagaca ccctcttctc tgcgagttcc cacctggggt ccctttttggg   120 gaccgaacac tggggtacag agagggaaga cctgggagac tgtcgcagtt tgatgaaaga   180
tatcaggaag tagaggggga cgaagtggaa tatgaggacc cagaagagga ggaagaggag   240
ggagaggggc gcggcagagt agcatccttg ctggccgcc ccaaaagaaa aagagttatt   300
gagtatgccc agcgccaggc cgccaacatt cgcgagagga agaggatgtt caacctaaac   360
gaggccttcg accagctgcg cagaaaggta cccaccttcg cttatgagaa gagactgtcg   420
aggatcgaga ccctccgctt ggccatcgtc tacatttcct tcatgaccga gctcctgcag   480
agcaaggagg aaaaggaggc cagctga                                       507
```

<210> SEQ ID NO 7
<211> LENGTH: 507
<212> TYPE: DNA
<213> ORGANISM: Artificial Sequence
<220> FEATURE:
<223> OTHER INFORMATION: Mouse T132E mutant Nato3 polynucleotide
<400> SEQUENCE: 7

```
atggccgcct atccagagag ctgcttggat gctaccgtgc tgaacttcgt agcagatctc    60
tctctggcct ctcccagaca ccctcttctc tgcgagttcc cacctggggt ccctttttggg   120 gaccgaacac tggggtacag agagggaaga cctgggagac tgtcgcagtt tgatgaaaga   180
tatcaggaag tagaggggga cgaagtggaa tatgaggacc cagaagagga ggaagaggag   240
ggagaggggc gcggcagagt agcatccttg ctggccgcc ccaaaagaaa aagagttatt   300
acttatgccc agcgccaggc cgccaacatt cgcgagagga agaggatgtt caacctaaac   360
gaggccttcg accagctgcg cagaaaggta cccgaattcg cttatgagaa gagactgtcg   420
aggatcgaga ccctccgctt ggccatcgtc tacatttcct tcatgaccga gctcctgcag   480
agcaaggagg aaaaggaggc cagctga                                       507
```

<210> SEQ ID NO 8
<211> LENGTH: 507
<212> TYPE: DNA
<213> ORGANISM: Artificial Sequence
<220> FEATURE:
<223> OTHER INFORMATION: Mouse S140D mutant Nato3 polynucleotide
<400> SEQUENCE: 8

```
atggccgcct atccagagag ctgcttggat gctaccgtgc tgaacttcgt agcagatctc    60
tctctggcct ctcccagaca ccctcttctc tgcgagttcc cacctggggt ccctttttggg   120 gaccgaacac tggggtacag agagggaaga cctgggagac tgtcgcagtt tgatgaaaga   180
tatcaggaag tagaggggga cgaagtggaa tatgaggacc cagaagagga ggaagaggag   240
ggagaggggc gcggcagagt agcatccttg ctggccgcc ccaaaagaaa aagagttatt   300
acttatgccc agcgccaggc cgccaacatt cgcgagagga agaggatgtt caacctaaac   360
gaggccttcg accagctgcg cagaaaggta cccaccttcg cttatgagaa gagactggac   420
aggatcgaga ccctccgctt ggccatcgtc tacatttcct tcatgaccga gctcctgcag   480
agcaaggagg aaaaggaggc cagctga                                       507
```

<210> SEQ ID NO 9
<211> LENGTH: 501
<212> TYPE: DNA
<213> ORGANISM: Artificial Sequence

```
<220> FEATURE:
<223> OTHER INFORMATION: Human T99E mutant Nato3 polynucleotide

<400> SEQUENCE: 9
atggcggcct atccggagag ctgcgtggac actacggtgc tggacttcgt cgcagacctg      60
tccctggcct ccccgagacg ccctctcctc tgcgacttcg cacccggggt ctccttgggg     120
gacccagccc ttgcgctccg agagggaaga cccaggagga tggcgcggtt tgaagagggg     180
gacccagaag aagaggagtg cgaagtggac caggggacg gagaagagga ggaggaagag      240
gagcgcggaa gaggtgtctc cctattaggc cgccccaaga ggaaaagggt gatcgagtac     300
gcccagcgcc aggccgccaa catccgcgaa aggaagcgga tgttcaacct caacgaggcc     360
tttgaccagc tgcggaggaa ggtgcccacg tttgcttacg agaaaaggct gtcccggatc     420 gagacccctcc gcctggccat cgtctatatc tccttcatga ccgagctctt ggagagctgt     480
gagaagaagg aaagcggctg a                                                501

<210> SEQ ID NO 10
<211> LENGTH: 501
<212> TYPE: DNA
<213> ORGANISM: Artificial Sequence
<220> FEATURE:
<223> OTHER INFORMATION: Human T130E mutant Nato3 polynucleotide

<400> SEQUENCE: 10
atggcggcct atccggagag ctgcgtggac actacggtgc tggacttcgt cgcagacctg      60
tccctggcct ccccgagacg ccctctcctc tgcgacttcg cacccggggt ctccttgggg     120
gacccagccc ttgcgctccg agagggaaga cccaggagga tggcgcggtt tgaagagggg     180
gacccagaag aagaggagtg cgaagtggac caggggacg gagaagagga ggaggaagag      240
gagcgcggaa gaggtgtctc cctattaggc cgccccaaga ggaaaagggt gatcacctac     300
gcccagcgcc aggccgccaa catccgcgaa aggaagcgga tgttcaacct caacgaggcc     360
tttgaccagc tgcggaggaa ggtgcccgag tttgcttacg agaaaaggct gtcccggatc     420 gagacccctcc gcctggccat cgtctatatc tccttcatga ccgagctctt ggagagctgt     480
gagaagaagg aaagcggctg a                                                501

<210> SEQ ID NO 11
<211> LENGTH: 501
<212> TYPE: DNA
<213> ORGANISM: Artificial Sequence
<220> FEATURE:
<223> OTHER INFORMATION: Human S138D mutant Nato3 polynucleotide

<400> SEQUENCE: 11
atggcggcct atccggagag ctgcgtggac actacggtgc tggacttcgt cgcagacctg      60
tccctggcct ccccgagacg ccctctcctc tgcgacttcg cacccggggt ctccttgggg     120
gacccagccc ttgcgctccg agagggaaga cccaggagga tggcgcggtt tgaagagggg     180
gacccagaag aagaggagtg cgaagtggac caggggacg gagaagagga ggaggaagag      240
gagcgcggaa gaggtgtctc cctattaggc cgccccaaga ggaaaagggt gatcacctac     300
gcccagcgcc aggccgccaa catccgcgaa aggaagcgga tgttcaacct caacgaggcc     360
tttgaccagc tgcggaggaa ggtgcccacg tttgcttacg agaaaaggct ggaccggatc     420 gagacccctcc gcctggccat cgtctatatc tccttcatga ccgagctctt ggagagctgt     480
gagaagaagg aaagcggctg a                                                501
```

<210> SEQ ID NO 12
<211> LENGTH: 168
<212> TYPE: PRT
<213> ORGANISM: Artificial Sequence
<220> FEATURE:
<223> OTHER INFORMATION: Mouse T101E Nato3 mutant polypeptide

<400> SEQUENCE: 12

```
Met Ala Ala Tyr Pro Glu Ser Cys Leu Asp Ala Thr Val Leu Asn Phe
1               5                   10                  15

Val Ala Asp Leu Ser Leu Ala Ser Pro Arg His Pro Leu Leu Cys Glu
            20                  25                  30

Phe Pro Pro Gly Val Pro Phe Gly Asp Arg Thr Leu Gly Tyr Arg Glu
        35                  40                  45

Gly Arg Pro Gly Arg Leu Ser Gln Phe Asp Glu Arg Tyr Gln Glu Val
    50                  55                  60

Glu Gly Asp Glu Val Glu Tyr Glu Asp Pro Glu Glu Glu Glu Glu Glu
65                  70                  75                  80

Gly Glu Gly Arg Gly Arg Val Ala Ser Leu Leu Gly Arg Pro Lys Arg
                85                  90                  95

Lys Arg Val Ile Glu Tyr Ala Gln Arg Gln Ala Ala Asn Ile Arg Glu
            100                 105                 110

Arg Lys Arg Met Phe Asn Leu Asn Glu Ala Phe Asp Gln Leu Arg Arg
        115                 120                 125

Lys Val Pro Thr Phe Ala Tyr Glu Lys Arg Leu Ser Arg Ile Glu Thr
    130                 135                 140

Leu Arg Leu Ala Ile Val Tyr Ile Ser Phe Met Thr Glu Leu Leu Gln
145                 150                 155                 160

Ser Lys Glu Glu Lys Glu Ala Ser
                165
```

<210> SEQ ID NO 13
<211> LENGTH: 168
<212> TYPE: PRT
<213> ORGANISM: Artificial Sequence
<220> FEATURE:
<223> OTHER INFORMATION: Mouse T132E Nato3 mutant polypeptide

<400> SEQUENCE: 13

```
Met Ala Ala Tyr Pro Glu Ser Cys Leu Asp Ala Thr Val Leu Asn Phe
1               5                   10                  15

Val Ala Asp Leu Ser Leu Ala Ser Pro Arg His Pro Leu Leu Cys Glu
            20                  25                  30

Phe Pro Pro Gly Val Pro Phe Gly Asp Arg Thr Leu Gly Tyr Arg Glu
        35                  40                  45

Gly Arg Pro Gly Arg Leu Ser Gln Phe Asp Glu Arg Tyr Gln Glu Val
    50                  55                  60

Glu Gly Asp Glu Val Glu Tyr Glu Asp Pro Glu Glu Glu Glu Glu Glu
65                  70                  75                  80

Gly Glu Gly Arg Gly Arg Val Ala Ser Leu Leu Gly Arg Pro Lys Arg
                85                  90                  95

Lys Arg Val Ile Thr Tyr Ala Gln Arg Gln Ala Ala Asn Ile Arg Glu
            100                 105                 110

Arg Lys Arg Met Phe Asn Leu Asn Glu Ala Phe Asp Gln Leu Arg Arg
        115                 120                 125

Lys Val Pro Glu Phe Ala Tyr Glu Lys Arg Leu Ser Arg Ile Glu Thr
    130                 135                 140
```

```
Leu Arg Leu Ala Ile Val Tyr Ile Ser Phe Met Thr Glu Leu Leu Gln
145                 150                 155                 160

Ser Lys Glu Glu Lys Glu Ala Ser
                165

<210> SEQ ID NO 14
<211> LENGTH: 168
<212> TYPE: PRT
<213> ORGANISM: Artificial Sequence
<220> FEATURE:
<223> OTHER INFORMATION: Mouse S140D Nato3 mutant polypeptide

<400> SEQUENCE: 14

Met Ala Ala Tyr Pro Glu Ser Cys Leu Asp Ala Thr Val Leu Asn Phe
1               5                   10                  15

Val Ala Asp Leu Ser Leu Ala Ser Pro Arg His Pro Leu Leu Cys Glu
            20                  25                  30

Phe Pro Pro Gly Val Pro Phe Gly Asp Arg Thr Leu Gly Tyr Arg Glu
        35                  40                  45

Gly Arg Pro Gly Arg Leu Ser Gln Phe Asp Glu Arg Tyr Gln Glu Val
    50                  55                  60

Glu Gly Asp Glu Val Glu Tyr Glu Asp Pro Glu Glu Glu Glu Glu Glu
65                  70                  75                  80

Gly Glu Gly Arg Gly Arg Val Ala Ser Leu Leu Gly Arg Pro Lys Arg
                85                  90                  95

Lys Arg Val Ile Thr Tyr Ala Gln Arg Gln Ala Ala Asn Ile Arg Glu
            100                 105                 110

Arg Lys Arg Met Phe Asn Leu Asn Glu Ala Phe Asp Gln Leu Arg Arg
        115                 120                 125

Lys Val Pro Thr Phe Ala Tyr Glu Lys Arg Leu Asp Arg Ile Glu Thr
    130                 135                 140

Leu Arg Leu Ala Ile Val Tyr Ile Ser Phe Met Thr Glu Leu Leu Gln
145                 150                 155                 160

Ser Lys Glu Glu Lys Glu Ala Ser
                165

<210> SEQ ID NO 15
<211> LENGTH: 166
<212> TYPE: PRT
<213> ORGANISM: Artificial Sequence
<220> FEATURE:
<223> OTHER INFORMATION: Human T99E Nato3 mutant polypeptide

<400> SEQUENCE: 15

Met Ala Ala Tyr Pro Glu Ser Cys Val Asp Thr Thr Val Leu Asp Phe
1               5                   10                  15

Val Ala Asp Leu Ser Leu Ala Ser Pro Arg Arg Pro Leu Leu Cys Asp
            20                  25                  30

Phe Ala Pro Gly Val Ser Leu Gly Asp Pro Ala Leu Ala Leu Arg Glu
        35                  40                  45

Gly Arg Pro Arg Arg Met Ala Arg Phe Glu Glu Gly Asp Pro Glu Glu
    50                  55                  60

Glu Glu Cys Glu Val Asp Gln Gly Asp Gly Glu Glu Glu Glu Glu Glu
65                  70                  75                  80

Glu Arg Gly Arg Gly Val Ser Leu Leu Gly Arg Pro Lys Arg Lys Arg
                85                  90                  95

Val Ile Glu Tyr Ala Gln Arg Gln Ala Ala Asn Ile Arg Glu Arg Lys
```

```
              100                 105                 110
Arg Met Phe Asn Leu Asn Glu Ala Phe Asp Gln Leu Arg Arg Lys Val
            115                 120                 125

Pro Thr Phe Ala Tyr Glu Lys Arg Leu Ser Arg Ile Glu Thr Leu Arg
        130                 135                 140

Leu Ala Ile Val Tyr Ile Ser Phe Met Thr Glu Leu Glu Ser Cys
145                 150                 155                 160

Glu Lys Lys Glu Ser Gly
                165
```

<210> SEQ ID NO 16
<211> LENGTH: 166
<212> TYPE: PRT
<213> ORGANISM: Artificial Sequence
<220> FEATURE:
<223> OTHER INFORMATION: Human T130E Nato3 mutant polypeptide

<400> SEQUENCE: 16

```
Met Ala Ala Tyr Pro Glu Ser Cys Val Asp Thr Thr Val Leu Asp Phe
1               5                  10                  15

Val Ala Asp Leu Ser Leu Ala Ser Pro Arg Arg Pro Leu Leu Cys Asp
            20                  25                  30

Phe Ala Pro Gly Val Ser Leu Gly Asp Pro Ala Leu Ala Leu Arg Glu
        35                  40                  45

Gly Arg Pro Arg Arg Met Ala Arg Phe Glu Glu Gly Asp Pro Glu Glu
    50                  55                  60

Glu Glu Cys Glu Val Asp Gln Gly Asp Gly Glu Glu Glu Glu Glu Glu
65                  70                  75                  80

Glu Arg Gly Arg Gly Val Ser Leu Leu Gly Arg Pro Lys Arg Lys Arg
                85                  90                  95

Val Ile Thr Tyr Ala Gln Arg Gln Ala Ala Asn Ile Arg Glu Arg Lys
            100                 105                 110

Arg Met Phe Asn Leu Asn Glu Ala Phe Asp Gln Leu Arg Arg Lys Val
        115                 120                 125

Pro Glu Phe Ala Tyr Glu Lys Arg Leu Ser Arg Ile Glu Thr Leu Arg
    130                 135                 140

Leu Ala Ile Val Tyr Ile Ser Phe Met Thr Glu Leu Glu Ser Cys
145                 150                 155                 160

Glu Lys Lys Glu Ser Gly
                165
```

<210> SEQ ID NO 17
<211> LENGTH: 166
<212> TYPE: PRT
<213> ORGANISM: Artificial Sequence
<220> FEATURE:
<223> OTHER INFORMATION: Human S138D Nato3 mutant polypeptide

<400> SEQUENCE: 17

```
Met Ala Ala Tyr Pro Glu Ser Cys Val Asp Thr Thr Val Leu Asp Phe
1               5                  10                  15

Val Ala Asp Leu Ser Leu Ala Ser Pro Arg Arg Pro Leu Leu Cys Asp
            20                  25                  30

Phe Ala Pro Gly Val Ser Leu Gly Asp Pro Ala Leu Ala Leu Arg Glu
        35                  40                  45

Gly Arg Pro Arg Arg Met Ala Arg Phe Glu Glu Gly Asp Pro Glu Glu
    50                  55                  60
```

Glu Glu Cys Glu Val Asp Gln Gly Asp Gly Glu Glu Glu Glu
65                  70                  75                  80

Glu Arg Gly Arg Gly Val Ser Leu Leu Gly Arg Pro Lys Arg Lys Arg
            85                  90                  95

Val Ile Thr Tyr Ala Gln Arg Gln Ala Ala Asn Ile Arg Glu Arg Lys
            100                 105                 110

Arg Met Phe Asn Leu Asn Glu Ala Phe Asp Gln Leu Arg Arg Lys Val
            115                 120                 125

Pro Thr Phe Ala Tyr Glu Lys Arg Leu Asp Arg Ile Glu Thr Leu Arg
130                 135                 140

Leu Ala Ile Val Tyr Ile Ser Phe Met Thr Glu Leu Leu Glu Ser Cys
145                 150                 155                 160

Glu Lys Lys Glu Ser Gly
            165

<210> SEQ ID NO 18
<211> LENGTH: 56
<212> TYPE: PRT
<213> ORGANISM: Drosophila melanogaster

<400> SEQUENCE: 18

Gln Arg Arg Ala Ala Asn Ile Arg Glu Arg Arg Met Phe Asn Leu
1               5                   10                  15

Asn Glu Ala Phe Asp Lys Leu Arg Arg Lys Val Pro Thr Phe Ala Tyr
            20                  25                  30

Glu Lys Arg Leu Ser Arg Ile Glu Thr Leu Arg Leu Ala Ile Thr Tyr
            35                  40                  45

Ile Gly Phe Met Ala Glu Leu Leu
50                  55

<210> SEQ ID NO 19
<211> LENGTH: 56
<212> TYPE: PRT
<213> ORGANISM: Caenorhabditis elegans

<400> SEQUENCE: 19

Glu Arg Gln Thr Ala Ser Ile Arg Glu Arg Lys Arg Met Cys Ser Ile
1               5                   10                  15

Asn Val Ala Phe Ile Glu Leu Arg Asn Tyr Ile Pro Thr Phe Pro Tyr
            20                  25                  30

Glu Lys Arg Leu Ser Lys Ile Asp Thr Leu Asn Leu Ala Ile Ala Tyr
            35                  40                  45

Ile Asn Met Leu Asp Asp Val Leu
50                  55

<210> SEQ ID NO 20
<211> LENGTH: 56
<212> TYPE: PRT
<213> ORGANISM: Mus musculus

<400> SEQUENCE: 20

Gln Arg Gln Ala Ala Asn Ile Arg Glu Arg Lys Arg Met Phe Asn Leu
1               5                   10                  15

Asn Glu Ala Phe Asp Gln Leu Arg Arg Lys Val Pro Thr Phe Ala Tyr
            20                  25                  30

Glu Lys Arg Leu Ser Arg Ile Glu Thr Leu Arg Leu Ala Ile Val Tyr
            35                  40                  45

Ile Ser Phe Met Thr Glu Leu Leu

<210> SEQ ID NO 21
<211> LENGTH: 56
<212> TYPE: PRT
<213> ORGANISM: Homo sapiens

<400> SEQUENCE: 21

Gln Arg Gln Ala Ala Asn Ile Arg Glu Arg Lys Arg Met Phe Asn Leu
1               5                   10                  15

Asn Glu Ala Phe Asp Gln Leu Arg Arg Lys Val Pro Thr Phe Ala Tyr
            20                  25                  30

Glu Lys Arg Leu Ser Arg Ile Glu Thr Leu Arg Leu Ala Ile Val Tyr
        35                  40                  45

Ile Ser Phe Met Thr Glu Leu Leu
    50                  55

<210> SEQ ID NO 22
<211> LENGTH: 168
<212> TYPE: PRT
<213> ORGANISM: Artificial Sequence
<220> FEATURE:
<223> OTHER INFORMATION: T101E/T132E Mouse Nato3 mutant polypeptide

<400> SEQUENCE: 22

Met Ala Ala Tyr Pro Glu Ser Cys Leu Asp Ala Thr Val Leu Asn Phe
1               5                   10                  15

Val Ala Asp Leu Ser Leu Ala Ser Pro Arg His Pro Leu Leu Cys Glu
            20                  25                  30

Phe Pro Pro Gly Val Pro Phe Gly Asp Arg Thr Leu Gly Tyr Arg Glu
        35                  40                  45

Gly Arg Pro Gly Arg Leu Ser Gln Phe Asp Glu Arg Tyr Gln Glu Val
    50                  55                  60

Glu Gly Asp Glu Val Glu Tyr Glu Asp Pro Glu Glu Glu Glu Glu Glu
65                  70                  75                  80

Gly Glu Gly Arg Gly Arg Val Ala Ser Leu Leu Gly Arg Pro Lys Arg
                85                  90                  95

Lys Arg Val Ile Glu Tyr Ala Gln Arg Gln Ala Ala Asn Ile Arg Glu
            100                 105                 110

Arg Lys Arg Met Phe Asn Leu Asn Glu Ala Phe Asp Gln Leu Arg Arg
        115                 120                 125

Lys Val Pro Glu Phe Ala Tyr Glu Lys Arg Leu Ser Arg Ile Glu Thr
    130                 135                 140

Leu Arg Leu Ala Ile Val Tyr Ile Ser Phe Met Thr Glu Leu Leu Gln
145                 150                 155                 160

Ser Lys Glu Glu Lys Glu Ala Ser
                165

<210> SEQ ID NO 23
<211> LENGTH: 168
<212> TYPE: PRT
<213> ORGANISM: Artificial Sequence
<220> FEATURE:
<223> OTHER INFORMATION: T101E/S140D Mouse Nato3 mutant polypeptide

<400> SEQUENCE: 23

Met Ala Ala Tyr Pro Glu Ser Cys Leu Asp Ala Thr Val Leu Asn Phe
1               5                   10                  15

Val Ala Asp Leu Ser Leu Ala Ser Pro Arg His Pro Leu Leu Cys Glu

```
                20                  25                  30

Phe Pro Pro Gly Val Pro Phe Gly Asp Arg Thr Leu Gly Tyr Arg Glu
            35                  40                  45

Gly Arg Pro Gly Arg Leu Ser Gln Phe Asp Glu Arg Tyr Gln Glu Val
        50                  55                  60

Glu Gly Asp Glu Val Glu Tyr Glu Asp Pro Glu Glu Glu Glu Glu Glu
65                  70                  75                  80

Gly Glu Gly Arg Gly Arg Val Ala Ser Leu Leu Gly Arg Pro Lys Arg
                85                  90                  95

Lys Arg Val Ile Glu Tyr Ala Gln Arg Gln Ala Ala Asn Ile Arg Glu
                100                 105                 110

Arg Lys Arg Met Phe Asn Leu Asn Glu Ala Phe Asp Gln Leu Arg Arg
            115                 120                 125

Lys Val Pro Thr Phe Ala Tyr Glu Lys Arg Leu Asp Arg Ile Glu Thr
        130                 135                 140

Leu Arg Leu Ala Ile Val Tyr Ile Ser Phe Met Thr Glu Leu Leu Gln
145                 150                 155                 160

Ser Lys Glu Glu Lys Glu Ala Ser
                165

<210> SEQ ID NO 24
<211> LENGTH: 168
<212> TYPE: PRT
<213> ORGANISM: Artificial Sequence
<220> FEATURE:
<223> OTHER INFORMATION: T101E/T132E/S140D Mouse Nato3 mutant
      polypeptide

<400> SEQUENCE: 24

Met Ala Ala Tyr Pro Glu Ser Cys Leu Asp Ala Thr Val Leu Asn Phe
1               5                   10                  15

Val Ala Asp Leu Ser Leu Ala Ser Pro Arg His Pro Leu Leu Cys Glu
            20                  25                  30

Phe Pro Pro Gly Val Pro Phe Gly Asp Arg Thr Leu Gly Tyr Arg Glu
        35                  40                  45

Gly Arg Pro Gly Arg Leu Ser Gln Phe Asp Glu Arg Tyr Gln Glu Val
    50                  55                  60

Glu Gly Asp Glu Val Glu Tyr Glu Asp Pro Glu Glu Glu Glu Glu Glu
65                  70                  75                  80

Gly Glu Gly Arg Gly Arg Val Ala Ser Leu Leu Gly Arg Pro Lys Arg
                85                  90                  95

Lys Arg Val Ile Glu Tyr Ala Gln Arg Gln Ala Ala Asn Ile Arg Glu
                100                 105                 110

Arg Lys Arg Met Phe Asn Leu Asn Glu Ala Phe Asp Gln Leu Arg Arg
            115                 120                 125

Lys Val Pro Glu Phe Ala Tyr Glu Lys Arg Leu Asp Arg Ile Glu Thr
        130                 135                 140

Leu Arg Leu Ala Ile Val Tyr Ile Ser Phe Met Thr Glu Leu Leu Gln
145                 150                 155                 160

Ser Lys Glu Glu Lys Glu Ala Ser
                165

<210> SEQ ID NO 25
<211> LENGTH: 166
<212> TYPE: PRT
<213> ORGANISM: Artificial Sequence
<220> FEATURE:
```

<223> OTHER INFORMATION: T99E/T130E Human Nato3 mutant polypeptide

<400> SEQUENCE: 25

Met Ala Ala Tyr Pro Glu Ser Cys Val Asp Thr Thr Val Leu Asp Phe
1               5                   10                  15

Val Ala Asp Leu Ser Leu Ala Ser Pro Arg Arg Pro Leu Leu Cys Asp
            20                  25                  30

Phe Ala Pro Gly Val Ser Leu Gly Asp Pro Ala Leu Ala Leu Arg Glu
        35                  40                  45

Gly Arg Pro Arg Arg Met Ala Arg Phe Glu Glu Gly Asp Pro Glu Glu
    50                  55                  60

Glu Glu Cys Glu Val Asp Gln Gly Asp Gly Glu Glu Glu Glu Glu Glu
65                  70                  75                  80

Glu Arg Gly Arg Gly Val Ser Leu Leu Gly Arg Pro Lys Arg Lys Arg
                85                  90                  95

Val Ile Glu Tyr Ala Gln Arg Gln Ala Ala Asn Ile Arg Glu Arg Lys
            100                 105                 110

Arg Met Phe Asn Leu Asn Glu Ala Phe Asp Gln Leu Arg Arg Lys Val
        115                 120                 125

Pro Glu Phe Ala Tyr Glu Lys Arg Leu Ser Arg Ile Glu Thr Leu Arg
    130                 135                 140

Leu Ala Ile Val Tyr Ile Ser Phe Met Thr Glu Leu Leu Glu Ser Cys
145                 150                 155                 160

Glu Lys Lys Glu Ser Gly
                165

<210> SEQ ID NO 26
<211> LENGTH: 166
<212> TYPE: PRT
<213> ORGANISM: Artificial Sequence
<220> FEATURE:
<223> OTHER INFORMATION: T99E/S138D Human Nato3 mutant polypeptide

<400> SEQUENCE: 26

Met Ala Ala Tyr Pro Glu Ser Cys Val Asp Thr Thr Val Leu Asp Phe
1               5                   10                  15

Val Ala Asp Leu Ser Leu Ala Ser Pro Arg Arg Pro Leu Leu Cys Asp
            20                  25                  30

Phe Ala Pro Gly Val Ser Leu Gly Asp Pro Ala Leu Ala Leu Arg Glu
        35                  40                  45

Gly Arg Pro Arg Arg Met Ala Arg Phe Glu Glu Gly Asp Pro Glu Glu
    50                  55                  60

Glu Glu Cys Glu Val Asp Gln Gly Asp Gly Glu Glu Glu Glu Glu Glu
65                  70                  75                  80

Glu Arg Gly Arg Gly Val Ser Leu Leu Gly Arg Pro Lys Arg Lys Arg
                85                  90                  95

Val Ile Glu Tyr Ala Gln Arg Gln Ala Ala Asn Ile Arg Glu Arg Lys
            100                 105                 110

Arg Met Phe Asn Leu Asn Glu Ala Phe Asp Gln Leu Arg Arg Lys Val
        115                 120                 125

Pro Thr Phe Ala Tyr Glu Lys Arg Leu Asp Arg Ile Glu Thr Leu Arg
    130                 135                 140

Leu Ala Ile Val Tyr Ile Ser Phe Met Thr Glu Leu Leu Glu Ser Cys
145                 150                 155                 160

Glu Lys Lys Glu Ser Gly
                165

-continued

```
<210> SEQ ID NO 27
<211> LENGTH: 166
<212> TYPE: PRT
<213> ORGANISM: Artificial Sequence
<220> FEATURE:
<223> OTHER INFORMATION: T99E/T130E/S138D Human

<400> SEQUENCE: 27

Met Ala Ala Tyr Pro Glu Ser Cys Val Asp Thr Thr Val Leu Asp Phe
1               5                   10                  15

Val Ala Asp Leu Ser Leu Ala Ser Pro Arg Arg Pro Leu Leu Cys Asp
                20                  25                  30

Phe Ala Pro Gly Val Ser Leu Gly Asp Pro Ala Leu Ala Leu Arg Glu
            35                  40                  45

Gly Arg Pro Arg Arg Met Ala Arg Phe Glu Glu Gly Asp Pro Glu Glu
        50                  55                  60

Glu Glu Cys Glu Val Asp Gln Gly Asp Gly Glu Glu Glu Glu Glu Glu
65                  70                  75                  80

Glu Arg Gly Arg Gly Val Ser Leu Leu Gly Arg Pro Lys Arg Lys Arg
                85                  90                  95

Val Ile Glu Tyr Ala Gln Arg Gln Ala Ala Asn Ile Arg Glu Arg Lys
                100                 105                 110

Arg Met Phe Asn Leu Asn Glu Ala Phe Asp Gln Leu Arg Arg Lys Val
            115                 120                 125

Pro Glu Phe Ala Tyr Glu Lys Arg Leu Asp Arg Ile Glu Thr Leu Arg
        130                 135                 140

Leu Ala Ile Val Tyr Ile Ser Phe Met Thr Glu Leu Leu Glu Ser Cys
145                 150                 155                 160

Glu Lys Lys Glu Ser Gly
                165
```